United States Patent [19]

Harreus et al.

[11] Patent Number: 5,116,971
[45] Date of Patent: May 26, 1992

[54] SUBSTITUTED-1,4-DIAZEPINES

[75] Inventors: Albrecht Harreus, Ingelheim am Rhein; Karl-Heinz Weber; Werner Stransky, both of Gau-Algesheim; Gerhard Walther, Bingen; Gojko Muacevic, Ingelheim am Rhein; Jorge C. Stenzel, Munich; Wolf-Dietrich Bechtel, Appenheim, all of Fed. Rep. of Germany

[73] Assignee: Boehringer Ingelheim KG, Ingelheim am Rhein, Fed. Rep. of Germany

[21] Appl. No.: 584,815

[22] Filed: Sep. 19, 1990

Related U.S. Application Data

[63] Continuation of Ser. No. 33,966, Apr. 1, 1987, abandoned.

[30] Foreign Application Priority Data

Apr. 1, 1986 [DE] Fed. Rep. of Germany ....... 3610848

[51] Int. Cl.$^5$ ................ C07D 495/14; C07D 487/04; A61K 31/55
[52] U.S. Cl. .................................. 540/362; 540/560; 540/563; 540/564; 540/565; 540/566
[58] Field of Search ............... 540/562, 563, 564, 565, 540/566, 498, 499, 560

[56] References Cited

U.S. PATENT DOCUMENTS 4,968,794 11/1990 Weber et al. ................... 540/560

Primary Examiner—Robert T. Bond
Attorney, Agent, or Firm—D. E. Frankhouser; M-E. M. Timbers; A. R. Stempel

[57] ABSTRACT

The invention relates to new 1,4-diazepines of the general formula

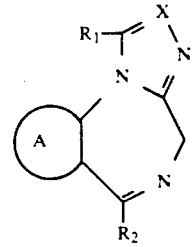

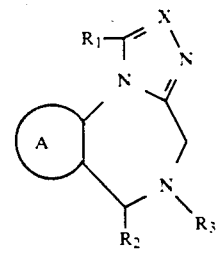

in which
$R_1$, $R_2$, $R_3$, X and A have the meaning indicated in the specification.

The new compounds are intended for use for the treatment of pathological states and diseases in which PAF (platelet activating factor) is involved.

32 Claims, No Drawings

SUBSTITUTED-1,4-DIAZEPINES

This is a continuation of application Ser. No. 033,966, filed Apr. 1, 1987 now abandoned.

This invention relates to novel substituted 1,4-diazepines and the optically active isomers, racemates and where possible the physiologically acceptable acid addition salts thereof, to methods of preparing these compounds, to pharmaceutical compositions containing them as active ingredients, and to therapeutic methods of using them. By virtue of their PAF-antagonistic action, the subject compounds may be used to treat an individual having a disorder responsive to said action.

More particularly, the present invention relates to novel substituted 1,4-diazepines represented by the formulas:

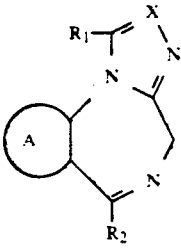

I or

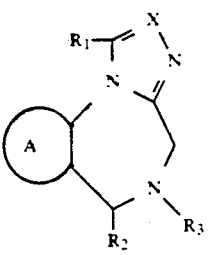

II in which

X is CH, C-halogen or nitrogen;

$R_1$ is hydrogen, branched or unbranched $C_1-C_4$ alkyl optionally substituted by hydroxyl or halogen, cyclopropyl, $C_1-C_4$ alkoxy, preferably methoxy, or halogen, preferably chlorine or bromine;

$R_2$ is phenyl, α-pyridyl or phenyl substituted, preferably in the 2-position, with one or more substituents selected from methyl, methoxy, halogen, preferably chlorine or bromine, nitro and trifluoromethyl;

$R_3$ is hydrogen or branched or unbranched $C_1-C_4$ alkyl;

A is a fused-on ring of the formula

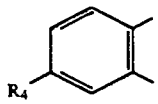

a or

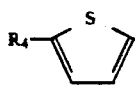

b in which $R_4$ is a functional side-chain of the formula

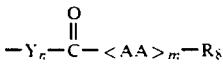

in which n is zero or an integer from 1 to 8;

m is an integer from 1 to 3, preferably 1;

Y is a branched or unbranched alkyl with n carbons;

<AA> is an amino acid linked N-terminally or a peptide, or, preferably, an amino acid of the formula

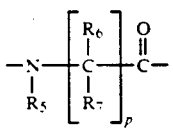

in which

P is an integer from 1 to 8;

$R_5$ is hydrogen or branched or unbranched $C_1-C_5$ alkyl; and $R_6$ and $R_7$, which can be identical or different, are each hydrogen, branched or unbranched alkyl, alkenyl or alkynyl having 1 to 10 carbons, $C_3-C_6$ cycloalkyl, aryl or arylalkyl, said "aryl" being optionally substituted with at least one substituent selected from hydroxyl, halogen, amino, and branched or unbranched $C_1-C_4$ alkylamino, di-($C_1-C_4$)alkylamino or $C_1-C_4$ alkoxy, [it being possible when $R_6$ and/or $R_7$ denotes alkyl for $R_6$ and/or $R_7$ to be optionally substituted one or more times by hydroxyl, alkoxy, $C_3-C_7$ cycloalkyl, halogen, amino (which can optionally be substituted once or twice by branched or unbranched alkyl, alkoxycarbonyl or aralkoxycarbonyl, in each case having 1 to 4 carbon atoms in the alkyl chain), guanidino, ureido, cycloxy, carboxy, alkoxycarbonyl, cyano, aminocarbonyl, alkylcarbonyl, mercapto, alkylthio, benzylthio, alkylsulfinyl, alkylsulfonyl, 3-indolyl, imidazolyl, pyrazolyl, or an amide of the formula

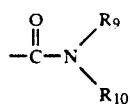

in which $R_9$ and $R_{10}$, which can be identical or different, are each hydrogen, branched or unbranched alkyl, alkenyl or alkynyl having 1 to 4 carbons, $C_1-C_4$ alkyl substituted by amino which can optionally be substituted once or twice with branched or branched $C_1-C_4$ alkyl in the alkyl chain or once with hydroxyl, or $R_9$ and $R_{10}$ together form a 3- to 6-membered ring optionally containing one or more additional heteroatoms selected from nitrogen, oxygen or sulphur, said rings being optionally substituted with at least one branched or unbranched $C_1-C_4$ alkyl, preferably methyl];

$R_8$ is an amino of the formula

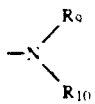

or branched or unbranched $C_1$-$C_4$ alkoxy or $C_1$-$C_4$ alkylthio, the alkyl of which can be optionally substituted with an amino of the formula

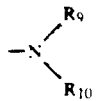

in which $R_9$ and $R_{10}$, singly or together, are as previously defined $R_6$ and $R_7$, taken together optionally form a 3- to 7-membered ring which can optionally contain at least one heteroatom selected from nitrogen, oxygen or sulphur, said rings being optionally substituted with at least one branched or unbranched $C_1$-$C_4$ alkyl, preferably methyl; or $R_5$, taken together with $R_6$ or $R_7$, optionally form a 4- to 7-membered ring which can optionally contain at least one heteroatom selected from nitrogen, oxygen or sulphur, said rings being optionally substituted with at least one branched or unbranched $C_1$-$C_4$ alkyl; or $R_6$ or $R_7$, taken together with $R_8$, optionally form a 5- to 7-membered ring of the formula

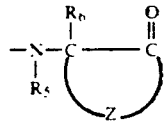

in which $R_5$ and $R_6$ are as previously defined; and

Z is one of the heteroatoms, nitrogen, oxygen or sulphur, said ring being optionally substituted with branched or unbranched $C_1$-$C_4$ alkyl, preferably methyl;

and the optically active isomers, racemates and physiologically acceptable acid addition salts thereof.

In subgeneric aspects, the invention comprehends the following classes of compounds.

A. Preferred compounds of the above formulas I or II are those in which:

X is CH or nitrogen;

$R_1$, $R_3$ and A are respectively defined hereinabove;

$R_2$ is phenyl or substituted phenyl as hereinabove defined (particularly halophenyl, preferably 2-halophenyl and most preferably 2-chlorophenyl);

$R_4$ is a functional side-chain of the formula

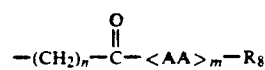

in which n, m and $R_8$ are respectively defined hereinabove (particularly m=1); and <AA> is an amino acid of the formula

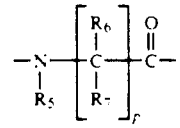

in which p is 1 or 2; and $R_5$, $R_6$ and $R_7$ are respectively defined hereinabove; and the optically active isomers, racemates, and physiologically acceptable acid addition salts thereof.

B. Particularly preferred compounds of formulas I or II are those in which:

X is CH or nitrogen;

A is as defined hereinabove;

$R_1$ is hydrogen, methyl, ethyl, cyclopropyl, methoxy, ethoxy, or halogen (preferably chlorine or bromine);

$R_2$ is phenyl or 2-halophenyl (preferably 2-chlorophenyl);

$R_3$ is hydrogen or methyl (preferably hydrogen);

$R_4$ is a functional side-chain of the formula

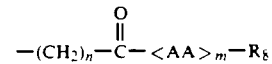

in which n is zero or 1 when A is the fused-on ring of formula a, and is zero or an integer from 1 to 8 when A is the fused-on ring of formula b;

m is 1 or 2 (preferably m=1);

$R_8$ is as defined in hereinabove;

<AA> is an amino acid of the formula

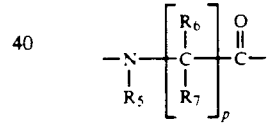

in which p is 1 or 2; and $R_5$, $R_6$ and $R_7$ are respectively defined hereinabove; and the optically active isomers, racemates and physiologically acceptable acid addition salts thereof.

C. Very particularly preferred compounds of formulas I or II are those in which:

X is CH or nitrogen (preferably nitrogen);

A is as defined hereinabove;

$R_1$ is hydrogen, methyl, ethyl, cyclopropyl, methoxy, ethoxy, chlorine or bromine (preferably methyl or methoxy);

$R_2$ is phenyl or 2-halophenyl (preferably 2-chlorophenyl);

$R_3$ is hydrogen;

$R_4$ is a functional side-chain of the formula

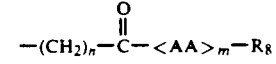

in which n is zero or 1 when A is the fused-on ring of formula a (preferably n TM zero), and zero, 1, 2, 3, or 4 when A is the fused-on ring of formula b (preferably n=zero, 1 or 2);
m is 1 or 2 (particularly m=1);
<AA> is an α-amino acid of the formula

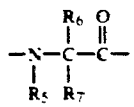

in which $R_5$ is hydrogen;

$R_6$ and $R_7$, which can be identical or different, are each hydrogen, branched or unbranched alkyl having 1 to 8 carbons (preferably 1 to 5 carbons) optionally substituted with $C_1$-$C_4$ alkoxycarbonyl, $C_1$-$C_4$ alkylthio or $C_1$-$C_4$ alkylsulfonyl;

$R_8$ is $C_1$-$C_4$ alkoxy (preferably methoxy or ethoxy) or an amino of the formula

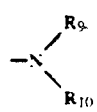

in which $R_9$ and $R_{10}$, which can be identical or different, are each branched or unbranched alkyl or alkenyl having 1 to 4 carbons, or $R_9$ and $R_{10}$ together form a 5- or 6-membered ring optionally containing an additional heteroatom selected from nitrogen or oxygen, said rings being optionally substituted with at least one branched or unbranched $C_1$-$C_4$ alkyl (particularly methyl);

and the optically active isomers, racemates and physiologically acceptable acid addition salts thereof.

Unless otherwise indicated, halogen denotes fluorine, chlorine, bromine or iodine; alkyl denotes a branched or unbranched alkyl having 1 to 4 carbon atoms, such as, for example, methyl, ethyl, n-propyl, isopropyl, n-butyl, tert-butyl and the like; alkoxy denotes the corresponding $C_1$-$C_4$ alkoxies; aryl preferably denotes phenyl; arylalkyl preferably denotes benzyl; and acyl preferably denotes acetyl.

The abreviation <AA> denotes an amino acid or a peptide, of which the preferred amino acids are: Aad, —Abu, —Aca, Ach, Acp, β-Aib, —Ala, Ama, Apm, Apr, Arg, Asn, Asu, Cys, Gln, Glu, His, Ser, Hyl, Hyp, 3-Hyp, Ise, Lys, Nle, Nva, Pec, Phe, Phg, Pic, Pro, Tle, Pyr, Ser, thr, Tyr or Trp; and the particularly preferred amino acids are: Ala, β-Ala, Gly, Val, Met, Asp, Sar, Met-($O_2$), Aib, Abu, Ile or Leu.

The indicated amino acid abbreviations are identical to those used in the literature, (for example Houben Weyl, Lehrbuch der organischen Chemie) but do not relate exclusively to the L-configuration but also relate to the optically active D-amino acids and to their racemates.

The invention also embraces processes for the preparation of the new compounds and of pharmaceutical compositions containing these compounds. Unless otherwise indicated, the formula symbols in the hereinafter process description are as initially indicated in the specification.

The new compounds of formula I can be prepared by processes analogous to those described in peptide chemistry (for example in Houben-Weyl, Methoden der organischen Chemis, Vol. 15, published by Georg Thieme-Verlag, Stuttgart, 1974) from the corresponding carboxylic acids of formula IIIa or IIIb

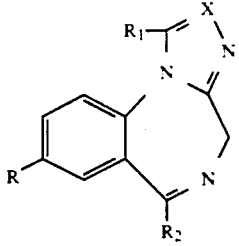

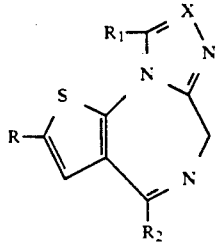

in which the radicals $R_1$, $R_2$ and X each have the previously indicated meaning, and R denotes a side-chain of the general formula $$-Y_n-COOH$$

a) wherein n and Y each have the previously indicated meaning, by reaction with a compound of following formula IV $$H-<AA>_m-R_8 \quad (IV)$$

in which <AA>, $R_8$ and m each have the previously indicated meaning, in the presence of a carbodiimide, carbonyldiimidazol, sulfonyldiimidazol, or b) by conversion of the free acid of formula III into a reactive acid derivative such as, for example, an acid halide, imidazolide or mixed anhydride and then reacting same with a compound of formula IV.

The reaction of the acid with compound IV is carried out in the presence of a carbodiimide, for example cyclohexylcarbodiimide, in an inert organic solvent such as, for example, dimethylformamide, tetrahydrofuran, dioxan and their mixtures, at temperatures between 0° C. and the boiling point of the reaction mixture, preferably between 0° C. and room temperature.

The reaction of the amino component of formula IV with an acid halide, mixed anhydride or imidazolide prepared from formula III is carried out in an inert organic solvent such as, for example, dimethylformamide, tetrahydrofuran, dioxane and mixtures thereof, at temperatures between −20° C. and the boiling point of the reaction mixture, preferably between 0° C. and room temperature, there being addition, where appropriate, of an acid binding agent such as, for example, sodiumcarbonate, sodiumbicarbonate or a tertiary organic base, for example pyridine or triethylamine.

The condensation reactions can be catalysed by methods known per se by addition of N,N-dimethylaminopyridine.

The acid halide or mixed anhydride of formula III is obtained from the free acid in a conventional manner, for example, by reaction of the acid with oxalyl chloride or in reaction with ethyl chloroformate.

The imidazolide is obtained in the conventional manner, for example, by reaction of the acid with 1,1'-carbonyldiimidazole.

The new compounds of formula I in which $R_8$ denotes an amino group $$-N\begin{array}{c}R_9\\\\R_{10}\end{array}$$

in which $R_9$ and $R_{10}$ have the previously described meaning, can also be prepared by reaction, by known processes, of a compound of following formula V, Va Vb $R = -Y_n-CO-<AA>_m-OH$ with an amine of the formula $$H-N\begin{array}{c}R_9\\\\R_{10}\end{array}$$

in which $R_9$ and $R_{10}$ are as defined above.

The free carboxylic acids of formula V are obtained by hydrolysis of compounds of formula I in which $R_8$ denotes alkoxy or alkylthio, in a conventional manner, for example by alkaline hydrolysis in a mixture of tetrahydrofuran and water at room temperature.

The esters and amides of amino acids, and the esters and amides of peptides, of formula IV are obtained by processes customary in peptide chemistry as are described, for example, in Houben-Weyl, Vol. 15.

The carboxylic acids of the formulas IIIa/b, some of which are new, are obtained by hydrolysis of the corresponding ester VIa/b, for example, with sodium hydroxide in a mixture of tetrahydrofuran and water.

VIa

VIb $R = -Y_n-COOR'$, $R' = $ lower alkyl.

Some of the intermediate compounds of formula VIa/b are new. The compound VI in which X denotes N are prepared by known and analogous processes.

Starting from the thione VII

VII $A = $ a b $R = -Y_n-COOR'$ reaction is carried out either a) with a hydrazide of the following formula VIII $R_1CONHNH_2$      VIII in which $R_1$ has the previously described meaning, with the exception of halogen, or b) with hydrazine to give a compound of the following formula IX

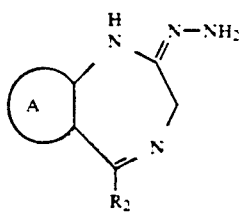

and then with an acid halide of the general formula

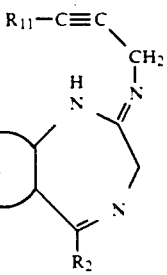

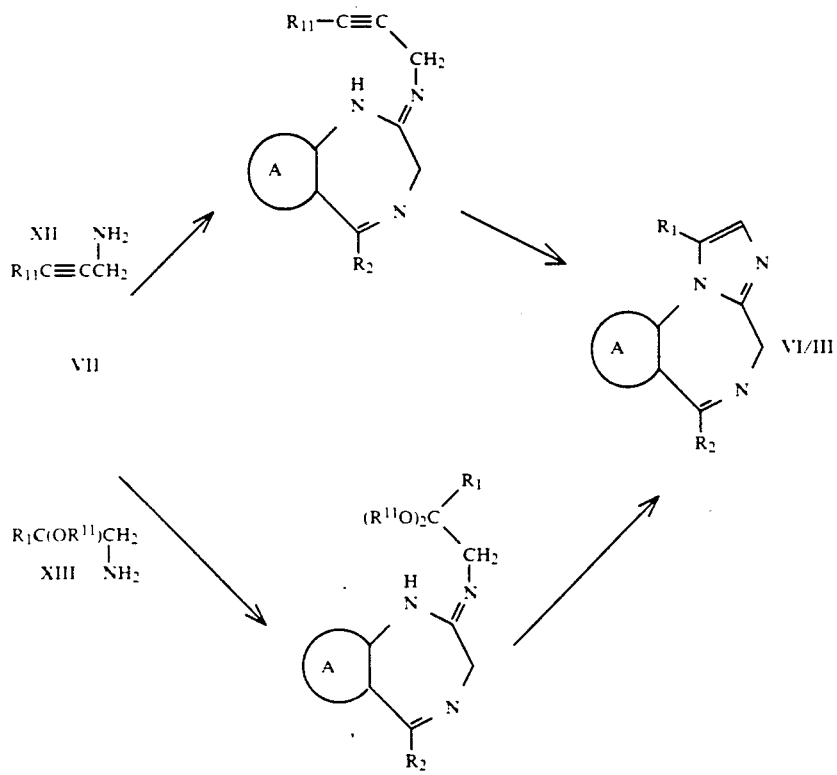

$R_1-\overset{O}{\overset{\|}{C}}-Hal$ in which Hal denotes a halogen atom, preferably chlorine, and $R_1$ has the previously described meaning, or with an orthoester of the following formula XI $R_1C(OR'')_3$  XI in which R" denotes a lower alkyl group.

The reaction of the thione VII with the hydrazide VIII by process a), or with the hydrazine IX by process b), is carried out in an inert organic solvent such as, for example, dioxane, dimethylformamide tetrahydrofuran or a suitable hydrocarbon, such as, for example, benzene or toluene, at temperatures between room temperature and the boiling point of the reaction mixture.

The hydrazino-1,4-diazepines which are thus produced can be isolated by conventional process or can be directly processed further.

The further reaction with an acid halide X or an orthoester XI is carried out in an inert organic solvent such as, for example, halogenated hydrocarbons or aliphatic ethers.

The end products are isolated by known methods, such as, for example, by crystallisation.

Compounds of formula I in which X denotes CH are prepared from the corresponding carboxylic acids of formula III in which $R_1$ $R_2$ and A have the previously indicated meaning and X is CH, in the manner described previously. Compounds of formula III or VI with X=CH are obtained from the thione of the general formula VII by reaction with an aminoalkyne of formula XII in which $R_{11}$ denotes hydrogen or alkyl, preferably hydrogen.

It is possible to prepare compounds of formula IIIa/b in which $R_1$ denotes alkyl, preferably methyl, by this process.

Another process comprises the reaction of the thione of formula VII with an α-aminoaldehyde dialkylacetal or α-aminoketone dialkylacetal of formula XIII, in which $R_1$ denotes hydrogen or $C_1$-$C_4$ alkyl, R' denotes lower alkyl, and $R_2$ and A each have the previously indicated meanings.

Analogous processes for the synthesis of an acetal of formula XIII, and an analogous process for the ring closure, are described in Swiss patent No. 580 099 and DE-OS 23 21 705. Analogous processes for the synthesis of the fused-on imidazole ring are likewise disclosed in DE-OS 23 21 705.

Under the customary acid reaction conditions of the cyclisation of the intermediates, if the functional sidechain of A has terminal ester groups it is possible for the latter simultaneously to be converted into the desired carboxylic acids.

Compounds of formula I in which $R_1$ denotes chlorine or bromine are prepared, for example, either from the compounds of formula I or from a compound of formula III with $R_1$=hydrogen by reaction with chlorine or bromine in pyridine. The latter are then converted as described into the compounds of formula I with $R_1$=Cl or Br.

The 1-alkoxy compounds are obtained, for example, from one of the above-mentioned chlorine or bromine compounds by reaction with the appropriate alkoxide.

An example of another method for the preparation of the alkoxy compounds of formula III is the reaction of the ester of formula VI with a halogen, and then reaction with the appropriate alkoxide.

The preparation of the thiones VII is described in Synthesis Scheme 3:

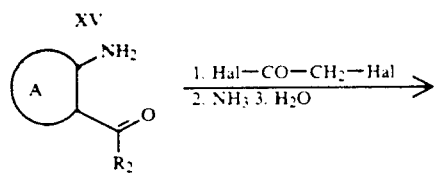

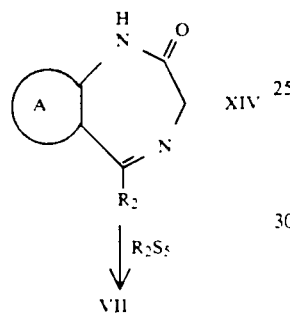

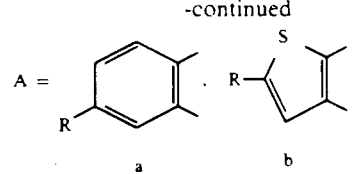

Some of the intermediate compounds detailed in the synthetic scheme have already been described or can be prepared in analogous processes from known compounds. Thus, for example, the synthesis of the benzodiazepine XIVa, n=0, is described in Sternbach et al. Helv. Chim. Acta 186, 1720 (1960) and the synthesis of the thienodiazepine XIVb for n=0 is disclosed in DOS 25 03 235 and by W. D. Bechtel and K. H. Weber, J. Pharm. Sci. 74, 1265 (1985) for n=2.

The preparation of the aminoketones of formula XVb in which $R_2$ has the previously indicated meanings is described in Synthetic Scheme 3':

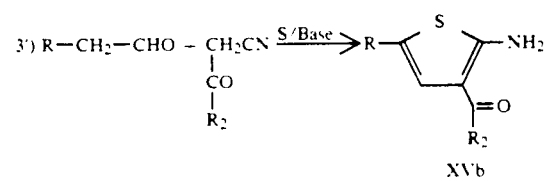

R can have the meaning of $R=Y_n$—COOR' or —$Y_n$—CH(COOR')$_2$.

If a dicarboxylic ester has been used, one of the carboxyl groups is eliminated at the stage of the amino ketone after the hydrolysis, as described in, for example, W. D. Bechtel and K. H. Weber, J. Pharm. Sci. 74, 1265 (1985).

The synthesis of the aminoketone XVa, in which $R_2$ is as defined previously is shown in Synthetic Scheme 4, by way of example for n=0 or 1.

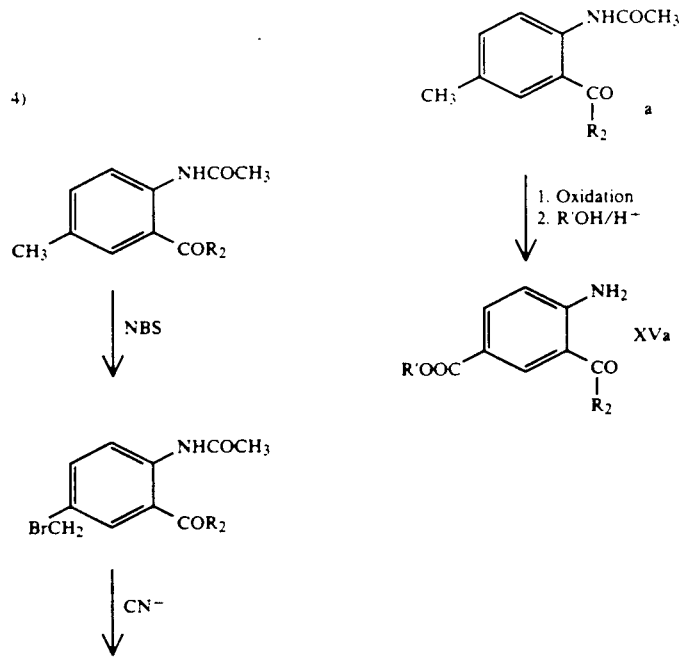

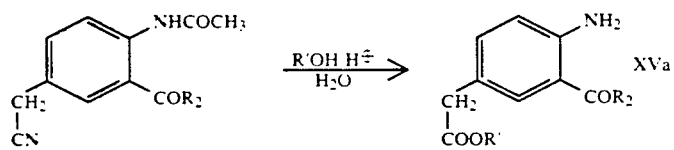

Some of the acetylated amino ketones (a) shown in Synthetic Scheme 4) are known; they are prepared by analogous processes as described, for example, by D. Walsh in Synthesis, 1980, 677-688. The oxidation of the methyl compound to give the acid is preferably carried out with potassium permanganate in a mixture of pyridine/water at temperatures between 20° C. and the boiling point of the reaction mixture, preferably at 90° C.

Where n=2, the synthesis is described, for example, by M. Zinic et al., J. Heterocycl. Chem. 4, 1225 (1977).

The compounds of formula I in which $R_8$ denotes an alkoxy group can alternatively be prepared, as shown in Synthetic Scheme 5, from the compounds of formula XV, where appropriate after preceding hydrolysis.

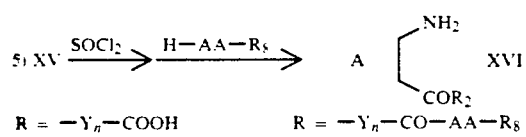

The acids of the amino ketone stage XV which have been prepared by the above-mentioned processes are converted into the acid halide, for example, using thionyl chloride in an inert organic solvent between room temperature and the boiling point of the reaction mixture. Subsequently the reaction is carried out with a N-terminal unblocked amino acid ester of the general formula IV, as already described above. The resulting compounds of formula XVI can then be converted, in analogy to the processes indicated as described before to the compounds of the general formula I.

The new compounds of formula II in which $R_3$ is hydrogen can be obtained in a conventional manner from the compounds of formula I by reduction with known reducing agents.

The reduction is carried out, for example with zinc in a mixture of glacial acetic acid and an inert organic solvent such as, for example, halogenated hydrocarbons, such as, for example dichloromethane, at temperatures between room temperature and the boiling point of the reaction mixture. Compounds of formula II in which $R_3$ denotes alkyl can be prepared from the above-mentioned compounds by alkylation.

Examples of compounds which can be prepared by one of the above-mentioned processes are the following:

The methylamide of N-{[1-methyl-6-(2-chlorophenyl)-4H-[1,2,4]triazolo[4,3-a][1,4]benzodiazepin-8-yl]-carbonyl}-D,L-alanine The dimethylamide of N-{[1-methyl-6-(2-chlorophenyl)-4H-[1,2,4]triazolo[4,3-a][1,4]benzodiazepin-8-yl]carbonyl}-1-aminocyclohexan-1-carboxylic acid The dimethylamide of N-{[1-methyl-6-(2-chlorophenyl)-4H-[1,2,4]triazolo[4,3-a][1,4]benzodiazepin-8-yl]carbonyl}-L-isoleucine.

The dimethylamide of N-{[1-methyl-6-(2-chlorophenyl)-4H-[1,2,4]triazolo[4,3-a][1,4]benzodiazepin-8-yl]carbonyl}-L-aspartic acid The morpholide of N-{[1-methyl-6-(2-chlorophenyl)-4H-[1,2,4]triazolo[4,3-a][1,4]benzodiazepin-8-yl]carbonyl}-D,L-β-aminoisobuteric acid The morpholide of N-{2-[1-methoxy-6-(2-chlorophenyl)-4H-[1,2,4]triazolo[4,3-a][1,4]benzodiazepin-8-yl]propionyl}-L-serine The diethylamide of N-{2-[1-methoxy-6-(2-chlorophenyl)-4H-[1,2,4]triazolo[4,3-a][1,4]benzodiazepin-8-yl]propionyl}-α-methylalanine The morpholide of N-{2-[4-(2-chlorophenyl)-9-methyl-6H-thieno[3,2-f]imidazo[1,2-a][1,4]diazepin-2-yl]propionyl}-glycine The diethylamide of N-{2-[1-methyl-6-phenyl-4H-[1,2,4]triazolo[4,3-a][1,4]benzodiazepin-8-yl]propionyl]-L-alanine The dimethylamide of N-{3-[4-(2-chlorophenyl)-9-methyl-6H-thieno[3,2-f]imidazo[1,2-a][1,4]diazepin-2-yl]-2-methylpropionyl}-D,L-α-aminopropionic acid.

The compounds according to the invention have a PAF-antagonistic action. As is known, PAF (platelet activating factor) is the phospholipid acetyl glyceryl ether phosphoryl-cholin (AGEPC) which is known as a potent lipid mediator and is released by animal and human proinflammatory cells. Cells of this type principally comprise basophilic and neutrophilic granulocytes, macrophages (from blood and tissue) and platelets which are involved in inflammatory reactions.

In pharmacological experiments, PAF shows broncho-constriction, a reduction in blood pressure, initiation of platelet aggregation and a proinflammatory action.

These experimentally detectable actions of PAF indicate, directly or indirectly, the possible functions of this mediator in anaphylaxis, in the pathophysiology of bronchial asthma and, generally, in inflammation.

PAF antagonists are required in order, on the one hand, to elucidate further pathophysiological functions of this mediator in animals and humans and, on the other hand, to treat pathological states and diseases in which PAF is involved Examples of the indications for a PAF antagonist are inflammatory processes of the trachyobronchial tree (acute and chronic bronchitus, bronchial asthma) or the kidneys (glomerulonephritis), anaphylactic states, allergies and inflammations of the mucosa and the skin (for example psoriasis) and states of shock caused by sepsis, endotoxins or burns. Other important indications for a PAF antagonist are lesions and inflammations of the mucosa of the stomach and intestines, such as, for example, gastritis, peptic ulcer in general but, in particular, gastric ulcer and dodenal ulcer.

The compounds according to the invention are also suitable for the treatment of the following diagnoses: obstructive pulmonary disorders such as, for example, bronchial hyperreactivity, inflammatory airway diseases such as, for example, chronic bronchitis; cardiovascular disorders such as, for example, polytrauma, anaphylaxis, arteriosclerosis; inflammatory intestinal disorders, EPH gestosis (edema-protein uria hypertension), disorders of extracorporal circulation, ischaemic diseases, inflammatory and immunological diseases, immunomodulation in the transplantation of foreign tissues, immunomodulation in leukaemia; the spread of metastases, for example in bronchial neoplasia, disorders of the CNS, for example, migraine, agoraphobia (panic disorder), in addition, the compounds according to the invention prove to be cytoprotective and organoprotective, for example for neuroprotection, for example in liver cirrhosis, DIC (diseminated intravascular coagulation); PAF-associated interaction with tissue hormones (autocoid hormones), lymphokines and other mediators.

The PAF-antagonistic action of a few benzodiazepines has been disclosed, compare E. Kornecki et al., Science 226, 1454-1456 (1984). The $IC_{50}$ (concentration for 50% inhibition of aggregation), measured by the method described below, was 14 μm for alprazolam, and the $IC_{50}$ for triazolam was 9 μm. However, these compounds, which are proven tranquillisers or hypnotics and are commercially available, are, because of their pronounced sedative action and despite their good PAF-antagonistic action, in many cases unsuitable for use as PAF antagonists in therapy.

In contrast, the compounds according to the invention lack the sedative effect, whereas the PAF-antagonistic action is considerably better than that of the known benzodiazepines.

The PAF-antagonistic effect of some of the compounds of formulae I and II has been tested on the basis of the inhibition of blood platelet aggregation in vitro.

I. In vitro investigations: inhibition of blood platelet aggregation

To determine the PAF-antagonistic action of substances, use was made of the aggregation of human platelets induced in vitro by PAF. To obtain platelet-rich plasma (PRP), blood is taken from an uncompressed vein using a plastic syringe containing 3.8% strength sodium citrate solution. The ratio between sodium citrate solution and blood is 1:9. After careful mixing, the citrated blood is centrifuged at 150×g (1200 rpm) for 20 minutes. The platelet aggregation is measured by the method worked out by Born and Cross (G. V. R. Born and M. J. Cross, J. Physiol. 168, 178 (1963)), with PAF being added to the continuously stirred PRP to initiate the aggregation. The test substance is added in a volume of 10 ul in each case 2-3 minutes before initiation of the aggregation. The solvents used are either distilled water, ethanol and/or dimethyl sulphoxide. Blanks contain corresponding volumes of these solvents. After the initial absorption has been recorded (2-3 minutes), aggregation is induced with PAF ($5 \times 10^{-8}$M). To assess the effects of substances, use is made of the maximum of the first aggregation wave. The maximum absorption rate (=maximum aggregation×100%) induced by PAF is, in each case, simultaneously checked in a parallel mixture (=blank in one channel of the two-channel aggregometer) for each test mixture (second channel) and used as the 100% value. The aggregation obtained under the influence of the test substance is reported as 100%.

Each test substance is examined at concentrations of $10^{-3}$ to $10^{-8}$M, with n=4 samples in each case, for an inhibitory action on the platelet aggregation induced by PAF. Then a concentration-effect graph is plotted on the basis of 3 concentrations, and the $IC_{50}$ (concentration for 50% inhibition of aggregation) is determined.

The IC values for compounds of the general formulae I or II are generally in the range below 9 μm.

Table A lists in vitro investigations on the inhibition of blood platelet aggregation as described above.

TABLE A

| Compound | $IC_{50}$ μM |
|---|---|
| Alprazolam | 14 |
| Triazolam | 9 |
| Example No. of table I | |
| 2 | 0.9 |
| 4 | 0.7 |
| 5 | 1.2 |
| 11 | 3.5 |
| 12 | 1.1 |
| 15 | 0.9 |
| 16 | 0.4 |
| 18 | 8.1 |
| 21 | 1.9 |
| 27 | 0.7 |
| 28 | 1.9 |
| 33 | 2.5 |
| 35 | 0.9 |
| 48 | 0.6 |

The compounds of formulas I or II can be administered to warm-blooded animals topically, orally, parenterally or by inhalation. For this purpose, the compounds are present as active ingredients in customary presentations, for example in formulations which essentially consist of an inert pharmaceutical vehicle and an effective dose of the active compound, such as, for example, tablets, coated tablets, capsules, wafers, powders, solutions, suspensions, inhalation aerosols, ointments, emulsions, syrups, suppositories. etc., preferably in unit-dosage form. An effective dose of the compounds according to the invention for oral use is between 1 and 200 mg/dose, preferably between 20 and 100 mg dose, and for parenteral use, for example intravenous or intramuscular, between 0.01 and 50 mg/dose, preferably between 0.1 and 10 mg/dose. Solutions containing 0.01 to 1.0, preferably 0.1 to 0.5, weight/volume percent of active compound may be used for inhalation.

The Examples which follow serve to illustrate the invention in detail:

EXAMPLE 1

Morpholide of N-{[1-methyl-6-(2-chlorophenyl)-4H-[1,2,4]triazolo[4,3-a][1,4]benzodiazepin-8-yl]carbonyl}glycine 1.1. 2,6-Dimethyl-4H-3,1-benzoxazin-4-one 45.5 g (0.3 mol) of 5-Methylanthranilic acid are refluxed together with 130 g of acetic anhydride for 3 hours. After the solvent has been evaporated in vacuo, the residue is dissolved in 200 ml of dichloromethane, and the solution is filtered through silica gel. The concentrated filtrate is induced to crystallise with isopropyl ether.

Yield: 48 g (84% of theory), melting point 124°-125° C.

1.2. 2-Acetamido-5-methyl-2'-chlorobenzophenone

The Grignard reagent prepared from 312.5 g (1.63 mol) of 2-bromochlorobenzene and 39.6 g (1.63 mol) of magnesium in 1.2 liters of anhydrous ether is added dropwise, in 2.5 hours, to a stirred solution of 270 g (1.54 mol) of 2,6-dimethyl-4H-3,1-benzoxazin-4-one in 4 liters of absolute ether at room temperature. The mixture is then allowed to react for a further 2 hours at the same temperature. While cooling in ice, the mixture is cautiously hydrolysed with 2N hydrochloric acid and then the aqueous phase is separated off. The organic phase is washed first with dilute sodium hydroxide solution and then with water. The organic phase is dried and concentrated. The resulting residue is induced to crystallise with isopropyl ether.

Yield: 194 g (44% of theory), melting point 156°–158° C.

An alternative synthesis of 2-acetamido-5-methyl-2'-chlorobenzophenone is carried out analogously to Sternbach et al., Helv. Chim. Acta 186, 1720 (1963).

Analogously to a literature method [JACS 78, 4842 (1978)]. 82.5 g of boron trichloride is passed into 350 ml of dichloroethane while cooling in ice. To this are added dropwise, within 30 min. 68 g of 4-methylaniline dissolved in 400 ml of dichloroethane. Then 175 g of 2-chlorobenzonitrile are added to the reaction mixture (internal temperature 0° C.) and then, in portions, 94 g of aluminium chloride, during which the temperature rises to 20° C., and then the mixture is refluxed for 6 hours. After cooling, decomposition is carried out with 400 ml of 2N hydrochloric acid, cooling in an ice bath, and the mixture is heated at 80° C. for 30 min. and then, after cooling, extracted with dichloromethane. After the organic phase has been dried and concentrated, the residue is chromatographed on silica gel using dichloromethane/methanol (98:2) as mobile phase, and 67.5 g of 2-amino-5-methyl-2'-chlorobenzophenone are obtained as crude product. This is acetylated with 22 g of acetyl chloride and 23 g of triethylamine in 600 ml of dichloromethane. After the working up, the title compound is obtained in a yield of 57.1 g of m.p. 156°–158° C.

1.3. 4-Acetamido-3-(2-chlorobenzoyl)benzoic acid 159.2 g (0.533 mol) of 2-acetamido-5-methyl-2'-chlorobenzophenone are suspended in a mixture of 550 ml of pyridine and 1100 ml of water, the suspension is heated to 90° C. and, while stirring vigorously, 226.9 g (1.44 mol) of potassium permanganate are added in portions within 3 hours. Then the hot reaction mixture is filtered and, after cooling, extracted several times with ethyl acetate. The aqueous phase is adjusted to pH 3 with hydrochloric acid, and the crystals which separate out during this are isolated.

Yield: 103.5 g (59% of theory), m.p. 272°–273° C. (Sternbach et al., m.p. 263°–265° C.).

1.4. Methyl 4-amino-3-(2-chlorobenzoyl)benzoate 103.5 g (0.326 mol) of the benzoic acid prepared above are refluxed in 1000 ml of methanol and 18.6 g of para-toluenesulphonic acid hydrate for 24 hours. After concentration to one quarter of the reaction volume, the crystals which have separated out are filtered off with suction and washed first with methanol and then isopropyl ether.

Yield: 84.5 g (90% of theory), m.p. 155°–156° C.

1.5. Methyl 4-bromoacetamido-3-(2-chlorobenzoyl)benzoate 84.5 g (0.29 mol) of the amino compound described above are dissolved in 800 ml of anhydrous dioxane, and 24 ml of pyridine are added. Then 26.3 ml (0.3 mol) of bromoacetal bromide, dissolved in 100 ml of anhydrous dioxane, are added dropwise. After 24 hours, the mixture is filtered through kieselguhr, the filtrate is concentrated, and the residue is recrystallised from acetone.

Yield: 100 g (84% of theory), m.p. 136° C.

1.6. Methyl 1,3-dihydro-5-(2-chlorophenyl)-2H-[1,4]-benzodiazepin-2-one-7-carboxylate Gaseous ammonia is passed for 3 hours into 114 g (0.278 mol) of the bromoacetyl compound for example 1.5 dissolved in 1500 ml of ethyl acetate at room temperature. The mixture is then left to react further for 24 hours while stirring. After filtration through silica gel and evaporation of the solvent, the amino compound is obtained as an oil. The crude product thus obtained is dissolved in 1.2 liters of toluene and, after addition of 200 g of SiO$_2$, is refluxed with a water trap for 1.5 hours. The mixture is then filtered, and the resulting diazepinone is extracted with a heated mixture of methanol and dichloromethane. The combined extracts are evaporated to dryness in vacuo, and the residue is recrystallised from ethyl acetate.

Yield: 77.9 g (91% of theory), m.p. 245°–248° C.

1.7. Methyl 1,3-dihydro-5-(2-chlorophenyl)-2H-[1,4]benzodiazepin-2-thione-7-carboxylate 37.5 g (0.114 mol) of the above mentioned diazepinone in 350 ml of pyridine are heated at 65° C. with 32 g of phosphorus pentasulphide for 5 hours. The reaction mixture is then stirred into 700 ml of a 20% strength sodium chloride solution, then diluted with water, and the precipitated benzodiazepine-2-thione is filtered off and washed with ethanol. The crude product, 39 g. can be reacted further without further purification. Recrystallisation from isopropyl ether results in the thione of m.p. 246°–248° C.

1.8. 8-Carboxy-6-(2-chlorophenyl)-1-methyl-4H-[1,2,4]triazolo[4,3-a][1,4]benzodiazepine 10 g of Hydrazine hydrate are added to 39 g (0.113 mol) of the thione in 500 ml of tetrahydrofuran, and the mixture is stirred at room temperature for 30 minutes. The suspension is filtered through kieselguhr, and the filtrate is evaporated to dryness. The crude product is dissolved in 540 ml of absolute ethanol; after addition of 106 ml of triethyl orthoacetate, the mixture is heated at the reflux temperature for 1 hour. After evaporation of the solvent and recrystallisation from ethyl acetate, 33 g of 6-(2-chlorophenyl)-1-methyl-7-(methoxycarbonyl)-4H-[1,2,4]triazolo[4,3-a][1,4]-benzodiazepine of m.p. 169°–173° C. are obtained. An analytically pure substance is obtained by recrystallisation from methanol/ether: m.p. 178°–180° C.

The compound can also be prepared from the benzodiazepine-2-thione with acetyl hydrazide.

33 g (0.09 mol) of the above ester are hydrolysed with 4.5 g (0.113 mol) of sodium hydroxide in a mixture of 120 ml of water, 400 ml of tetrahydrofuran and 400 ml of methanol at the boiling point for 1 hour. The mixture is concentrated, the residue is taken up in water, and the solution is acidified with glacial acetic acid. The crystals which have separated out are isolated and dried.

Yield: 28.6 g (90% of theory), m.p. 350°–352° C.

1.9. Morpholide of N-{[1-methyl-6-(2-chlorophenyl)-4H-[1,2,4]triazolo[4,3-a][1,4]-benzodiazepin-8-yl]carbonyl}glycine 1.75 g (5 mmol) of 8-carboxy-6-(2-chlorophenyl)-1-methyl-4H-[1,2,4]triazolo[4,3a][1,4]-benzodiazepine are introduced into a solvent mixture comprising 40 ml of anhydrous tetrahydrofuran and 10 ml of anhydrous dimethylformamide. The 0.82 g (5 mmol) of 1,1'-carbonyldiimidazole is added, and the mixture is stirred at room temperature for 1 hour. Then 0.56 g (5.5 mmol) of triethylamine and 1 g (5.6 mmol) of glycinmorpholide hydrochloride. After 3 days, the mixture is concentrated, the residue is taken off in dichloromethane/water and the solution is extracted several times with water. The organic phase is concentrated, and the resulting residue is triturated with ethyl acetate.

Yield: 2.1 g (87% of theory) of amorphous substance, m.p. 159°-162° C.

EXAMPLE 2

Morpholide of N-{[1-Methyl-6-(2-chlorophenyl)-4H-[1,2,4]triazolo[4,3-a][1,4]benzodiazepin-8-yl]-acetyl}glycine 2.1. 2-Acetamido-5-bromomethyl-2'-chlorobenzophenone 52.8 g (0.18 mol) of 2-acetamido-5-methyl-2'-chlorobenzophenone are dissolved in 185 ml of anhydrous carbon tetrachloride and, while cooling, 32 g (0.18 mol) of N-bromosuccinimide are added. Then 0.4 g of azo-bis-isobutyronitrile is added, and the mixture is cautiously heated. After stirring at the reflux temperature for 8 hours, the mixture is filtered, and the filtrate is washed twice with dilute sodium hydroxide solution and then with water. The organic phase is concentrated, and the residue is recrystallised from ethanol. Yield 30 g (45% of theory) of the bromo compound, m.p. 108° C.

2.2 4-Acetamido-3-(2-chlorobenzoyl)phenylacetonitrile 9.8 g (0.2 mol) of sodium cyanide are added to 65 g (0.18 mol) of 2-acetamido-5-bromomethyl-2'-chlorobenzophenone in 85 ml of anhydrous triethylene glycol at room temperature, and the mixture is stirred for one hour. It is then heated at 100° C. for 1.5 hours for further reaction. After cooling, 1000 ml of water are added, the mixture is extracted several times with dichloromethane, and the organic phase is washed with water, dried and concentrated. The oily residue is purified by column chromatography on silica gel with dichloromethane/methanol.

Yield: 32.2 g (58% of theory) of oil.

2.3. Ethyl 4-amino-3-(2-chlorobenzoyl)-phenylacetate 32.2 g (0.1 mol) of 4-acetamido-3-(2-chlorobenzoyl)-phenylacetonitrile are dissolved in 340 ml of absolute ethanol. While cooling in ice, dry gaseous hydrogen chloride is passed in for one hour. The mixture is subsequently refluxed for 30 minutes and then stirred at room temperature for 24 hours. Five times the amount of water is added to the reaction mixture, which is left to stand for 15 minutes. Extraction with dichloromethane, drying and concentration of the organic phase is followed by working out by chromatography on silica gel results in 20.9 g (64% of theory) of the title compound as an oil.

2.4. Ethyl 4-bromoacetamido-3-(2-chlorobenzoyl)-phenyl-acetate 20.9 g (0.66 mol) of ethyl 4-amino-3-(2-chlorobenzoyl)-phenylacetate are dissolved in 170 ml of anhydrous dioxane. First 5.2 ml of absolute pyridine are added and then 13.3 g (0.066 mol) of bromoacetylbromide are added dropwise at room temperature and the mixture is stirred for 24 hours. The suspension is filtered through Kieselgur. The Kieselgur is washed with ether, and the combined filtrates are concentrated in vacuo. The resulting residue is induced to crystallise by addition of ethanol.

Yield: 24.6 g (85% of theory), m p. 83°-85° C.

2.5. 5-(2-Chlorophenyl)-7-ethoxycarbonylmethyl-1,3-dihydro-2-oxo-2H-[1,4]benzodiazepine 24.6 g (0.56 mol) of the above bromoacetyl compound are dissolved in 280 ml of ethyl acetate. Gaseous ammonia is passed through the solution for 3 hours, and the mixture is stirred for a further 24 hours at 25° C. to complete the reaction. After filtration through Kieselgur the combined filtrates are concentrated, and the amino compound which results from this as an oil is immediately reacted further.

210 ml of toluene and 70 g of silica gel are added to the oil, and the reaction mixture is refluxed with a water trap for 3 hours. It is then filtered, the residue is washed several times with hot methanol, and the collected filtrates are evaporated to dryness. Purification is carried out by chromatographic working-up on silica gel with dichloromethane/methanol (97:3) as eluant, and the 1,4-benzodiazepin-2-one is obtained as an oil.

Yield: 19.3 g (97% of theory).

2.6. 5-(2-Chlorophenyl)-7-ethoxycarbonylmethyl-1,3-dihydro-2H-[1,4]benzodiazepine-2-thione In analogy to Example 1, from the benzodiazepinone described above the corresponding thione is obtained.

Yield: 13.3 g (66% of theory), mp. 148°-149° C.

2.7. 6-(2-Chlorophenyl)-8-ethoxycarbonylmethyl-1-methyl-4H-[1,2,4]triazolo[4,3-a][1,4]-benzodiazepine 13.3 g (36 mmol) of the above thione are, as described in Example 1, first converted into the hydrazino compound and, without further purification, reacted with triethyl orthoacetate. The triazolo compound is obtained after purification by chromatography on SiO$_2$ with dichloromethane/methanol (95/5) as eluant.

Yield 4.8 g; m.p. 156°-157° C.

2.8 6-(2-Chlorophenyl)-8-carboxymethyl-1-methyl-4H-[1,2,4]triazolo[4,3-a][1,4]benzodiazepine 3.2 g (8 mmol) of the triazolo compound (Example 2.7) is hydrolysed as described in Example 1. The acid is isolated at pH 3.5 and is induced to crystallise with isopropyl ether/ether. Yield: 2.3 g (77% of theory) of 6-(2-chlorophenyl)-8-(carboxymethyl)-1-methyl-4H-[1,2,4]triazolo[4,3-a]-[1,4]-benzodiazepine.

2.9 Morpholide of N-[1-methyl-6-(2-chlorophenyl)-4H-[1,2,4]triazolo[4,3-a][1,4]benzodiazepin-8-yl]-acetyl)glycine 1 g (2.7 mmol) of the 8-carboxymethyl compound prepared as in 2.8 is reacted with 0.54 g (3 mmol) of glycine morpholide hydrochloride and 1,1'-carbonyldiimidazole as described in Example 1. After working up and crystallisation from ethyl acetate/ether, 0.9 g (69% of theory) of the title compound is obtained as hemihydrate of melting point 157°-158° C.

EXAMPLE 3

Pyrrolidide of N-{[1-cyclopropyl-6-(2-chlorophenyl)-4H-[1,2,4]triazolo[4,3-a][1,4]benzodiazepin-8-yl]carbonyl}-L-alanine 3.1. 6-(2-Chlorophenyl)-1-cyclopropyl-8-methoxycarbonyl-[1,2,4]triazolo[4,3-a][1,4]benzodiazepine 7 g (20.3 mmol) of 5-(2-Chlorophenyl)-1,3-dihydro-7-methoxycarbonyl-2H-[1,4]benzodiazepine-2-thione and 3 g (30 mmol) of cyclopropanecarbohydrazide in 70 ml of dioxane are refluxed for 30 hours. The solvent is then removed in vacuo, and the residue is worked up by chromatography on silica gel with toluene/ethanol (9:1). Yield: 2.9 g (36% of theory) of 6-(2-chlorophenyl)-1-cyclopropyl-8-methoxycarbonyl[1,2,4]-triazolo[4,3-a][1,4]-benzodiazepine of melting point 185° C.

3.2.

The subsequent alkaline hydrolysis is carried out as described in Example 1. After acidification with glacial acetic acid, 2 g (90% of theory) of 8-carboxy-6-(2- chlorophenyl)-1-cyclopropyl-[1,2,4]triazolo[4,3-a]-[1,4]benzodiazepine are obtained in the form of crystals.

2 g (5.3 mmol) of the acid prepared in this way are introduced together with 0.8 g of 1-hydroxybenzotriazole, 0.6 g (6 mmol) of triethylamine and 1 g (5.6 mmol) of L-alanine pyrrolidide hydrochloride into 30 ml of N,N-dimethylformamide. After cooling to 0° C. 1.4 g (6.8 mmol) of dicyclohexylcarbodiimide are added, and the mixture is left to stir for 24 hours. The precipitated dicyclohexylurea is filtered off, the filtrate is evaporated to dryness and the residue is taken up in dichloromethane/water. The organic phase is extracted successively wit sodium bicarbonate solution and several times with water. Then the organic phase is dried with magnesium sulphate, and the residue from evaporation is recrystallised from ether/ethyl acetate. Yield: 2.6 g (96% of theory) of the title compound as the hemihydrate of melting point 170°-175° C., $[\alpha]_D^{20} = +20.5°$ (c=1, CHCl$_3$).

EXAMPLE 4

N{[1-Methyl-6-(2-chlorophenyl)-4H-imidazo[1,2-a]-[1,4]benzodiazepin-8-yl]carbonyl}-$\beta$-alanine methyl ester 4.1. 8-Carboxy-6-(2-chlorophenyl)-1-methyl-4H-imidazo-[1,2-a][1,4]benzodiazepine 1.6 g of Propargylamine are added dropwise to 3.1 g (9 mmol) of 5-(2-chlorophenyl)-7-methoxycarbonyl-[1,4]benzodiazepine-2-thione in 60 ml of anhydrous dioxane, and the mixture is then refluxed for 3 hours and stirred at room temperature for a further hour. The residue remaining after removal of the solvent in vacuo is taken up in dichloromethane/water. The aqueous phase is extracted once more with dichloromethane, the collected organic phases are washed with water, the solvent is removed, and the residue is recrystallised from ethyl acetate/ether. 2.1 g of 5-(2-chlorophenyl)-7-methoxycarbonyl-4H-2-propargylamino[1,4]-benzodiazepine of melting point 202°-205° C. are obtained.

1.6 g (4.37 mmol) of the compound thus obtained are heated in 7.5 ml of concentrated sulphuric acid at 100° C. for 10 minutes. After cooling, the mixture is poured onto ice, and the resulting mixture is made alkaline with ammonia solution and extracted with dichloromethane. The aqueous phase is adjusted to pH 5, and the precipitated 8-carboxy-6-(2-chloro-phenyl)-1-methyl-4H-imidazo[1,2-a][1,4]benzodiazepine is filtered off and dried. Yield: 1 g (65% of theory); m.p. 295°-297° C.

The organic phase is concentrated. 0.2 g (13% of theory) of 8-methoxycarbonyl-6-(2-chlorophenyl)-1-methyl-4H-imidazo[1,2-a][1,4]benzodiazepine of melting point 150°-151° C.

4.2.

1 g (2.9 mol) of the imidazobenzodiazepinecarboxylic acid is reacted with 1,1'-carbonyldiimidazole and 0.42 g (3 mmol) of $\beta$-alanine methyl ester hydrochloride and worked up analogously to Example 1. 0.25 g (20% of theory) of the title compound of melting point 226°-227° C. is obtained.

EXAMPLE 5

N-{[4-(2-Chlorophenyl)-9-methyl-6H-thieno[3,2-f]-[1,2,4]triazolo[4,3-a][1,4]diazepin-2-yl]carbonyl}-glycine ethyl ester 5.1. N-{[5-Amino-4-(2-chlorobenzoyl)thiophen-2-yl]carbonyl}glycine ethyl ester 14.0 g (50 mmol) of 5-amino-4-(2-chlorobenzoyl)-thiophene-2-carboxylic acid [the synthesis is carried out analogously to Hromatka et al., Monatsh. Chem. 104, 973 (1973)] are suspended in 250 ml of anhydrous dichloromethane. 8 ml of thionyl chloride are added dropwise, and the mixture is stirred at room temperature for 2.5 hours. It is then evaporated in vacuo, the residue is taken up in dichloromethane, and the solution is added dropwise to a mixture of 7 g (50 mmol) of glycine ethyl ester hydrochloride and 16 ml of triethylamine in 100 ml of anhydrous dichloromethane. After 1 our at room temperature the mixture is extracted with water. The residue from the concentrated organic phase is worked up by chromatography on silica gel. 8.1 g (44% of theory) of the title compound of melting point 216°-218° C. are obtained.

5.2. N-{[4-(2-Chlorophenyl)-thieno[2,3-b][1,4]-diazepin-7-on-2-yl]carbonyl}glycine ethyl ester 8.1 g (22.1 mmol) of the amino compound prepared as in 5.1 are introduced into 71 ml of dioxane and 1.8 ml of pyridine and converted, analogously to Example 1, by addition of 2.3 ml (26.2 mmol) of bromoacetyl bromide into the bromoacetyl compound. Yield: 9.9 g.

The crude product is dissolved in 170 ml of ethyl acetate, and then ammonia is passed into the solution for 2 hours, and working up is carried out as described in Example 1. The aminoacetamido compound is obtained as an oil, yield: 8 g.

Further reaction is carried out analogously to Example 1.6. The thienodiazepinone specified in the title is obtained in a yield of 3.1 g (29% of theory based on the amino compound used) of melting point 240°-242° C. (ethyl acetate/ether).

5.2.

3.1 g (7.6 mmol) of the above thienodiazepin-2-one are suspended in 25 ml of pyridine, 1.7 g (7.7 mmol) of phosphorus pentasulphide are added and the mixture is stirred at 60° C. for 1 hour. After working up as described in Example 1.7, 2.3 g (72% of theory) of the thienodiazepin-2-thione of melting point 220°-222° C. are obtained.

5.3.

The resulting thione is suspended in 20 ml of tetrahydrofuran, 0.3 ml of hydrazine hydrate is added and, after 0.5 hours at room temperature, the mixture is worked up. It is filtered, the residue is washed with tetrahydrofuran, and the collected filtrates are concentrated in vacuo. The hydrazino compound is obtained amorphous by trituration with ether (2.2 g (97% of theory)) and is stirred in a mixture of 12 ml of orthoacetic ester and 10 ml of absolute ethanol at 80° C. for 1 hour.

The solvent is removed, and the residue is chromatographed on silica gel using dichloromethane/ethyl acetate/methanol (7:2:1) as eluant. The homogeneous fractions are evaporated, and ethyl acetate is used to induce crystallisation. 1.2 g (52% of theory) of N-{[4-(2-chlorophenyl)-9-methyl-6H-thieno-[3,2-f][1,2,4]-triazolo[4,3-a]-[1,4]-diazepin-2-yl]carbonyl}glycine ethyl ester of melting point 251°-252° C. are obtained.

EXAMPLE 6

Morpholide of N-{[1-methyl-6-(2-chlorophenyl)-H-[1,2,4]-triazolo[4,3-a]benzodiazepin-8-yl]-carbonyl}-$\beta$-alanine 2.5 g (5.7 mmol) of N{[1-methyl-6-(2-chlorophenyl)-H-[1,2,4]triazolo[4,3-a]benzodiazepin-8-yl]carbonyl) $\beta$-alanine methyl ester, prepared analogously to Example 1, are dissolved in a mixture of 50 ml of tetrahydrofuran and 5 ml of water. Hydrolysis is carried out by dropwise addition of 1N sodium hydroxide solution, while stirring at room temperature, with consumption of the base being monitored with thymolphthalene as indicator. After completion of the reaction the mixture is neutralized with glacial acetic acid, the solvent is evaporated the residue is taken up in water, and the solution is acidified with 0.1N hydrochloric acid. The liberated N-{[1-methyl-6-(2-chlorophenyl)-4H-[1,2,4]-triazolo[4,3-a]benzodiazepin-8-yl]-carbonyl}-β-alanine is filtered off.

Yield: 2.1 g (84% of theory) of melting point 165°-167° C. (hydrate).

1.25 g (2.8 mmol) of the β-alanine derivative thus obtained are introduced into 30 ml of tetrahydrofuran and 9 ml of dimethylformamide, and 0.90 g (5.6 mmol) of 1,1'-carbonyldiimidazole is added. After 1 hour, 0.35 g (4 mmol) of morpholine dissolved in 20 ml of tetrahydrofuran is added dropwise, and the mixture is left to react for 3 days.

Subsequent working up as described in Example 1 provides the title compound which is obtained as crystals from ethyl acetate/ether.

Yield: 0.9 g (64% of theory), m.p. 218° C.

EXAMPLE 7

N{[1-Methyl-6-(2-chlorophenyl)-4H-[1,2,4]triazolo-[4,3-a][1,4]benzodiazepin-8-yl]carbonyl}glycinamide 1 g (2.35 mmol) of N-{[1-methyl-6-(2-chlorophenyl)-4H-[1,2,4]triazolo-[4,3-a][1,4]benzodiazepin-8-yl]-carbonyl}glycine methyl ester, prepared analogously to Example 1, is stirred in 50 ml of methanolic ammonia solution at 25° C. for 2 days. The solvent is then removed in vacuo, and the residue is recrystallised from ethyl acetate/ether. 0.7 g (73% of theory) of the glycine amide of melting point 185°-187° C. is obtained.

EXAMPLE 8

Morpholide of N-{[1-methyl-6-(2-chlorophenyl)-5,6-dihydro-4H-[1,2,4]triazolo[4,3-a][1,4]benzodiazepin-8-yl]carbonyl}glycine dihydrochloride 1 g (2.1 mmol) of the morpholide of N-{[1-methyl-6-(2-chlorophenyl)-4H-[1,2,4]triazolo-[4,3-a][1,4]-benzodiazepin-8-yl]carbonyl}glycine is dissolved in a mixture of 18 ml of dichloromethane and 18 ml of glacial acetic acid, 0.7 g (11 mmol) of zinc dust is added, and the mixture is left to react at room temperature for 16 hours. The suspension is filtered through kieselguhr washing with dichloromethane. The combined filtrates are made alkaline with dilute ammonia solution in the cold. The organic phase is separated off, and the aqueous phase is extracted twice more with dichloromethane. Concentration of the organic phase and dissolution of the resulting residue in ethanolic hydrochloric acid and precipitation with ether results in 0.7 g (58% of theory) of the title compound of melting point 218°-220° C. (hydrate).

EXAMPLE 9

Morpholide of N-methyl-N-{[1-methyl-6-(2-chlorophenyl)-4H-[1,2,4]triazolo[4,3-a][1,4]-benzodiazepin-8-yl]carbonyl}glycine 1.8 g (3.7 mmol) of the morpholide of N-[1-methyl-6-(2-chlorophenyl)-4H-[1,2,4]triazolo-[4,3-a][1,4]-benzodiazepin-8-yl]carbonyl}glycine are introduced into 100 ml of a mixture (10:1) of anhydrous tetrahydrofuran and dimethylformamide, and stirred with 0.25 g of a sodium hydride dispersion (60% in oil) at room temperature for 1 hour. After dropwise addition of 0.57 g (4 mmol) of methyl iodide dissolved in 10 ml of anhydrous tetrahydrofuran, the mixture is left to react at room temperature for 24 hours. The solvent is removed in vacuo, and water is cautiously added. The mixture is then extracted with dichloromethane and, after the usual working up and subsequent purification by chromatography, the title compound is obtained from ethyl acetate in the form of the hemihydrate of melting point 267°-269° C. in a yield of 0.5 g (27% of theory).

EXAMPLE 10

Morpholide of N-{[1-methyl-6-(2-chlorophenyl)-5,6-dihydro-4H-imidazo[1,2-a][1,4]benzodiazepin-8-yl]-carbonyl}glycine Starting from the morpholide of N-{[1-methyl-6-(2-chlorophenyl)-4H-imidazo[1,2-a][1,4]benzodiazepin-8-yl]carbonyl}glycine, the reduction is carried out as described in Example 8. The hydrate of the title compound of melting point 159°-162° C. is obtained.

EXAMPLE 11

Morpholide of N-methyl-N-{[4-(2-chlorophenyl)-9-methyl-6H-thieno[3,2-f][1,2,4]triazolo[4,3-a][1,4]-diazepin-2-yl]carbonyl}glycine Starting from the morpholide of N-{[4-(2-chlorophenyl)-9-methyl-6H-thieno[3,2-f][1,2,4]triazolo[4,3-a][1,4]diazepin-2-yl]carbonyl}glycine, alkylation is carried out analogously to Example 9. The amorphous hemihydrate of the title compound, of melting point 140°-143° C.) is obtained in 43% yield from ether.

EXAMPLE 12

Morpholide of N-{[1-bromo-6-(2-chlorophenyl)-4H-[1,2,4]triazolo[4,3-a][1,4]benzodiazepin-8-yl]-carbonyl}glycine 0.8 g (1.7 mmol) of the morpholide of N-{[6-(2-chlorophenyl)-4H-[1,2,4]triazolo[4,3-a][1,4]-benzodiazepin-8-yl]carbonyl}glycine prepared analogously to Example 1, is dissolved in 15 ml of anhydrous chloroform, and 0.2 g of pyridine and then 0.33 g of bromine are added. After the mixture has been stirred at room temperature for 4 days it is diluted with dichloromethane, and the organic phase is extracted several times with water, dried and concentrated. Column chromatography on silica gel with dichloromethane/methanol as eluant provides the title compound of melting point 168°-170° C. in a yield of 0.15 g.

EXAMPLE 13

Morpholide of N-{[1-methyl-6-(2-chlorophenyl)-5-methyl-5,6-dihydro-4H-[1,2,4]triazolo[4,3-a][1,4]-benzodiazepin-8-yl]carbonyl}glycine hydrochloride 1 g (2.1 mmol) of the morpholide of N-{[1-methyl-6-(2-chlorophenyl)-5,6-dihydro-4H-[1,2,4]triazolo-[4,3-a]-[1,4]benzodiazepin-8-yl]carbonyl}glycine is refluxed together with 0.7 g of formic acid and 0.37 g of formaline solution (37% strength) for 16 hours. The reaction mixture is acidified and treated with ether. The aqueous phase is separated off and made alkaline with concentrated ammonia solution. The base is extracted with dichloromethane and, after evaporation of the organic phase, is converted into the hydrochloride using ethanolic hydrochloric acid. 0.4 g (35% of theory) of the dihydrodiazepine is obtained in the form of the hydrochloride hydrate of melting point 180°–185° C.

EXAMPLE 14

Morpholide of
N-{[1-methoxy-6-(2-chlorophenyl)-4H-[1,2,4]triazolo[4,3-a][1,4]benzodiazepin-8-yl]-carbonyl}glycine 14.1. 1-Bromo-5-(2-chlorophenyl)-7-methoxycarbonyl-4H-[1,2,4]triazolo[4,3-a][1,4]benzodiazepine 6.7 g (19 mmol) of 5-(2-chlorophenyl)-8-methoxycarbonyl-4H-[1,2,4]triazolo[4,3-a][1,4]-benzodiazepine are dissolved in 130 ml of anhydrous chloroform. 2.2 g (28 mmol) of pyridine and 3.7 g (23 mmol) of bromine are successively added dropwise, and the reaction mixture is stirred at room temperature for 4 days. It is then extracted several times with water, the organic phase is dried, and the solvent is evaporated in vacuo. Purification by chromatography using dichloromethane/methanol (97:3) as eluant results in 2.2 g (27% of theory) of the bromo compound of melting point 171°–172° C.

14.2. 1.9 g (4.4 mmol) of the 1-bromotriazolobenzodiazepine compound are dissolved in 180 ml of methanol in which 2.3 g of potassium hydroxide have been dissolved, and the solution is stirred at 60° C. for 1 hour. After the solvent has been evaporated off in vacuo the residue is dissolved in dichloromethane. The solution is then extracted with water. The aqueous phase is acidified, and the resulting mixture of the 1-methoxy- and 1-hydroxy-8-carboxy-6-(2-chlorophenyl)-4H-[1,2,4]triazolo[4,3-a][1,4]-benzodiazepine is filtered off and dried.

Yield: 1.1 g.

The mixture is stirred in 15 ml of dimethylformamide with 0.5 g (2.8 mmol) of glycine morpholide hydrochloride, 0.3 g (3 mmol) of triethylamine and 0.4 g of 1-hydroxybenzotriazole, cooled to 0° C., and 0.7 g (3.4 mmol) of dicyclohexylcarbodiimide is added. After 24 hours the mixture is worked up analogously to Example 3. The homologues are separated by chromatography on silica gel using dichloromethane/ethyl acetate/methanol (70:25:5) as eluant. 0.25 g (19% of theory) of the morpholide of N-{[1-hydroxy-6-(2-chlorophenyl)-4H-[1,2,4]triazolo[4,3-a]-[1,4]-benzodiazepin-8-yl]carbonyl{glycine of melting point 190°–192° C. and 0.45 g of the title compound as the hemihydrate of melting point 179°–182° C.

EXAMPLE 15

Morpholide of
N-{[1-methyl-6-(2-chlorophenyl)-4H-[1,2,4]triazolo[4,3-a][1,4]benzodiazepin-8-yl]-carbonyl}-L-methionine sulphone 0.7 g (1.26 mmol) of the morpholide of N-{[1-methyl-6-(2-chlorophenyl)-4H-[1,2,4]triazolo[4,3-a]-[1,4]benzodiazepin-8-yl]carbonyl}-L-methionine is dissolved in 30 ml of anhydrous dichloromethane and, at 0° C., 0.6 g of m-chloroperbenzoic acid is added. After 24 hours at 0° C. a further 0.5 g of m-chloroperbenzoic acid is added, and the mixture is stirred for a further 3 hours at 25° C. It is diluted with 100 ml of dichloromethane and extracted by shaking successively with saturated sodium bisulphite solution, dilute sodium carbonate solution and water. The organic phase is concentrated, and the residue is purified by column chromatography. 0.2 g (26% of theory) of the sulphone is obtained as the hydrate of melting point 185°–187° C. by crystallisation with ether.

EXAMPLE 16

Morpholide of
N-{3-[4-(2-chlorophenyl)-9-methyl-6H-thieno[3,2-f][1,2,4]triazolo[4,3-a][1,4]diazepin-2-yl]propionyl}glycine 0.55 g (1.4 mmol) of 2-(2-carboxyethyl)-4-(2-chlorophenyl)-9-methyl-6H-thieno[3,2-f][1,2,4]triazolo[4,3-a][1,4]diazepine is suspended in 10 ml of anhydrous tetrahydrofuran, and 0.23 g (1.4 mmol) of 1,1'-carbonyldiimidazole and 5 ml of anhydrous dimethylformamide are added, and the mixture is stirred for 1 hour. 0.26 g (1.5 mmol) of glycine morpholide hydrochloride and 0.15 g (1.5 mmol) of triethylamine are successively added to the reaction mixture, which is left to stir at room temperature for 24 hours. After working up as described in Example 1, 0.4 g (56% of theory) of the title compound of melting point 201°–203° C. is obtained by recrystallisation from ethyl acetate.

The preparation of the starting compound, the corresponding carboxylic acid, is described in W. D. Bechtel and K. H. Weber, J. Pharm. Sci. 74, 1265 (1985).

EXAMPLE 17

L-1-Methyl-6-(2-chlorophenyl)-8-hexahydroazepin-2-on-3-yl-aminocarbonyl-4H-[1,2,4]triazolo[4,3-a][1,4]-benzodiazepine 3.5 g (0.01 mol) of 8-carboxy-6-(2-chlorophenyl)-1-methyl[1,2,4]triazolo-[4,3-a][1,4]benzodiazepine are suspended in 40 ml of dichloromethane. While cooling in ice, 2.5 g (0.02 mol) of oxalyl chloride are added dropwise, and the mixture is stirred at room temperature for 2 hours. It is then concentrated and subsequently distilled twice with anhydrous chloroform. The crystalline residue is triturated with petroleum ether and filtered off with suction. 3.7 g (100%) of 8-chlorocarbonyl-6-(2-chlorophenyl)-1-methyl[1,2,4]- triazolo[4,3-a][1,4]benzodiazepine of melting point 295°–297° C. are obtained.

3.7 g (0.01 mol) of acid chloride, 3.2 g (0.025 mol) of L-2-amino-ε-caprolactam and 0.2 g (0.0016 mol) of N,N-dimethyl-4-aminopyridine are stirred in 100 ml of anhydrous chloromethane for 16 hours. The emulsion is diluted with the same solvent and successively washed with dilute ammonia solution and water. After drying and concentration, the residue is taken up in dichloromethane/methanol and filtered through a little silica gel. The evaporated filtrates are crystallised with ether. 2.9 g (63% of theory) of the title compound of melting point 317° C. $[\alpha]_D^{20} = +38°$ (c=1, CHCl$_3$) are obtained.

Analogously to the processes described in the Examples, the following compounds of the general formula I or II are prepared:

TABLE I

| No. | Formula | X | $R_1$ | $R_2$ | $R_4$ | Mp °C, α |
|---|---|---|---|---|---|---|
| 1 | Ia | N | —CH$_3$ | 2-Cl-phenyl | —C(O)—NH—CH$_2$—C(O)—OC$_2$H$_5$ | 194 |
| 2 | Ia | CH | —CH$_3$ | " | —C(O)—NH—CH$_2$—CH$_2$—C(O)—OCH$_3$ | 226–227 |
| 3 | Ia | N | —CH$_3$ | " | —C(O)—NH—CH(CH$_2$—CH$_2$—S—CH$_3$)—C(O)—OCH$_3$ | 191–192 +11.1° L |
| 4 | Ia | N | —CH$_3$ | " | —C(O)—NH—CH$_2$—C(O)—N(morpholino) | 159–162 amorph |
| 5 | Ia | N | —CH$_3$ | " | —C(O)—NH—CH(CH$_2$—CO—OCH$_3$)—CO—OCH$_3$ | 175–176 −36.6° L |
| 6 | Ia | N | —CH$_3$ | " | —C(NH—CH$_2$—CH$_2$—C(O)—N(morpholino)) | amorph |
| 7 | Ia | N | —CH$_3$ | " | —C(O)—NH—CH$_2$—CH$_2$—C(O)—OCH$_3$ | 212 |
| 8 | Ia | N | —CH$_3$ | " | —C(O)—NH—CH$_2$—C(O)—NH$_2$ | 185–187 |
| 9 | Ia | N | —CH$_3$ | " | —C(O)—NH—CH$_2$—CH$_2$—C(O)—N(morpholino) | 218 |
| 10 | Ia | N | —CH$_3$ | 2-Cl-phenyl | —C(O)—NH—CH$_2$—C(O)—N(C$_2$H$_5$)$_2$ | 148–150 Semi-hydrate |
| 11 | Ia | N | —CH$_3$ | " | —C(O)—NH—(thiolan-2-one-3-yl) | 207–210 D,L |
| 12 | Ia | N | —CH$_3$ | " | —CH$_2$—C(O)—NH—CH$_2$—C(O)—N(morpholino) | 157–158 Semhdr. |
| 13 | Ia | N | —CH$_3$ | " | —C(O)—NH—CH(CH$_2$—CH(CH$_3$)$_2$)—C(O)—N(morpholino) | 152–155 hydrate +28.3° L |

TABLE I-continued

| No | Formula | X | R₁ | R₂ | R₄ | Mp °C, α |
|----|---------|---|-----|-----|-----|----------|
| 14 | Ia | N | —CH₃ | " | —C(=O)—NH—CH(CH₂—CH₂—S—CH₃)—C(=O)—N(morpholine) | 138-142 Semhydr −24.3° L |
| 15 | Ia | N | —CH₃ | " | —C(=O)—NH—CH(CH₂—CH₂—S—CH₃)—CO—OCH₃ | 192-193 −11.6° D |
| 16 | Ia | N | —CH₃ | " | —C(=O)—NH—CH(CH₂—CH(CH₃)₂)—C(=O)—N(C₂H₅)₂ | 155-158 Semhydr +11.8° L |
| 17 | Ia | N | —CH₃ | " | —C(=O)—NH—CH(CH₂—CH₂—S—CH₃)—C(=O)—N(C₂H₅)₂ | 120-124 Hydrate |
| 18 | Ia | N | —CH₃ | 2-Cl-phenyl | pyrrolidine(N—C=O)—CO—N(morpholine) | 174-177 Hydrate −24.5° L |
| 19 | Ia | N | —CH₃ | phenyl | —C(=O)—NH—CH₂—C(=O)—N(morpholine) | 186-187 Hydrate |
| 20 | Ib | N | —CH₃ | 2-Cl-phenyl | —C(=O)—NH—CH(CH₂—CH₂—S—CH₃)—C(=O)—OCH₃ | 142-145 +15.5° L |
| 21 | IIa | N | —CH₃ | " | —C(=O)—NH—CH₂—C(=O)—N(morpholine)  R₃ = H | 218-220 > 2HCl > H₂O |
| 22 | Ia | N | —CH₃ | " | —C(=O)—N(CH₃)—CH₂—C(=O)—N(morpholine) | 267-269 Semhydr |
| 23 | Ib | N | —CH₃ | " | —C(=O)—NH—CH(CH₂—CH(CH₃)₂)—C(=O)—OCH₃ | 183-184 +13.1° L |
| 24 | Ia | N | —CH₃ | " | —C(—(NH—CH₂—C)₃—N(morpholine)=O) | amorph |
| 25 | Ia | N | —CH₃ | " | —C(=O)—NH—CH(CH₂—CH₂—SO₂—CH₃)—C(=O)—N(morpholine) | 185-187 Hydrate +23.2° L |

TABLE I-continued

| No | Formula | X | R₁ | R₂ | R₃ | Mp °C, α |
|----|---------|---|----|----|----|----------|
| 26 | Ia | N | —CH₃ | 2-Cl-methylphenyl | —C(O)—NH—CH₂—C(O)—O—CH₂—CH₂—N(Et)(Et) | 157-160 ·2HCl |
| 27 | Ia | N | —CH₃ | " | —C(O)—NH—CH(CH(CH₃)₂)—C(O)—NH—CH(CH₃)₂ | 180-182 +8.7° L |
| 28 | Ib | N | —CH₃ | " | —C(O)—N(CH₃)—CH₂—C(O)—N(morpholino) | 140-143 |
| 29 | Ia | N | —CH₃ | " | —C(O)—N(H)—CH(CH(CH₃)₂)—C(O)—N(N-methylpiperazino) | 150-152 Semihydr +43.5° L |
| 30 | Ia | N | —CH₃ | " | —C(O)—NH—CH₂—C(O)—N(CH₃)₂ | 168-169 Semihydr |
| 31 | Ib | N | —CH₃ | " | —C(O)—NH—CH(CH₂—CH(CH₃)₂)—C(O)—N(morpholino) | 230-233 −23° L |
| 32 | Ia | N | —CH₃ | " | —C(O)—NH—CH₂—C(O)—NH—(CH₂)₂—N(C₂H₅)₂ | 133-137 Hydrate |
| 33 | Ia | N | —OCH₃ | " | —C(O)—NH—CH₂—C(O)—N(morpholino) | 179-182 |
| 34 | IIa | N | —CH₃ | " | —C(O)—NH—CH₂—C(O)—N(morpholino) | 180-185 Hydrate ·2HCl |
| 35 | Ia | N | cyclopropyl-2-Cl-methylphenyl | " | —C(O)—NH—CH(CH₃)—C(O)—N(pyrrolidino) | 170-175 Semihydr −20.5° L |
| 36 | Ia | CH | —CH₃ | " | —C(O)—NH—CH₂—C(O)—N(morpholino) | 153-156 |
| 37 | IIa | CH | —CH₃ | " | —C(O)—NH—CH₂—C(O)—N(morpholino) | 159-162 Hydrate |
| Ia | | N | —CH₃ | " | —C(O)—NH—CH(CH₂—CH₂—S—CH₃)—C(O)—N(morpholino), R₃ = H | 154-157 −23.7° D |

TABLE I-continued

| No. | Formula | X | $R_1$ | $R_2$ | $R_4$ | Mp °C, α |
|---|---|---|---|---|---|---|
| 39 | Ia | N | —CH₃ | " | —C(O)—NH—CH(CH₂—CH₂—S—CH₃)—C(O)—NH—CH₃ | amorph |
| 40 | Ia | N | —H | " | —C(O)—NH—CH₂—C(O)—N(morpholino) | 157–158 Hydrate |
| 41 | Ia | N | —Br | " | —C(O)—NH—CH₂—C(O)—N(morpholino) | 168–170 |
| 42 | Ia | N | —CH₃ | " | —(C(O)—NH—CH₂)₂—CH=CH₂ | 170–172 |
| 43 | Ib | N | —CH₃ | " | —CH₂—CH₂—C(O)—NH—CH(COOC₂H₅) | 187–188 |
| 44 | Ib | N | —CH₃ | " | —CH₂—C(O)—NH—CH₂—C(O)—N(morpholino) | amorph |
| 45 | Ib | N | —CH₃ | 2-Cl-phenyl | —C(O)—NH—CH₂—C(O)—OEt | 251–252 |
| 46 | Ib | N | —CH₃ | " | —C(O)—NH—CH₂—C(O)—N(morpholino) | 169–173 |
| 47 | Ib | N | —CH₃ | " | —CH₂—C(O)—NH—CH₂—C(O)—OEt | 179–182 |
| 48 | Ib | N | —CH₃ | " | —CH₂—CH₂—C(O)—NH—CH₂—C(O)—N(morpholino) | 201–203 |
| 49 | Ia | N | —CH₃ | " | —CO—NH—CH₂—COOCH₃ | 158–159 |
| 50 | Ia | N | —CH₃ | " | —CO—NCH₃—CH₂—COOCH₃ | amorph |
| 51 | Ia | N | —CH₃ | " | —CONHCH(CH₃)—CONHCH₃ | 191–192 |

α denotes [α]$_D^{20}$ and indicates the optical rotation of the compound, and L or D indicates the configuration of the amino acid.
In the table Et represents C₂H₅.

The following examples are of intermediate compound are prepared by the processes described in the Examples:

| Formula | X | $R_1$ | $R_2$ | $R_4$ | Mp. |
|---|---|---|---|---|---|
| Ia | N | CH₃ | phenyl | COOCH₃ | 239–240° C. |
| Ia | N | CH₃ | " | COOH | 352–355° C. |
| Ia | N | H | 2-Cl-phenyl | COOCH₃ | 239–240° C. |

-continued

| For-mula | X | R₁ | R₂ | R₄ | Mp |
|---|---|---|---|---|---|
| Ia | N | H | " | COOH | |
| Ia | N | CH₃ | " | CONHCH₂COOH | 190-192° C. Hydrate |
| Ib | N | CH₃ | " | CONHCH₂COOH | 212-216° C. |
| Ib | N | CH₃ | " | CO—L-Leu—OH | 185° C. |

N-{[2-Amino-3-(2-chlorobenzoyl)-thien-5-yl]carbonyl}-L-methionine methyl ester, M.p. 161°-162° C.

N-{[2-Amino-3-(2-chlorobenzoyl)-thien-5-yl]carbonyl}-L-leucine methyl ester, M.p. 178° C.

N-{[2-Bromoacetamido-3-(2-chlorobenzoyl)-thien-5-yl]-carbonyl}-L-methionine methyl ester, M.p. 122°-125° C. (decomposition).

N-{[2-Bromoacetamido-3-(2-chlorobenzoyl)-thien-5-yl]-carbonyl}-L-leucine methyl ester, M.p. 174°-177° C.

N-{[4-(2-chlorophenyl)-thieno[4,2-f][1,4]diazepin-7-on-2-yl]carbonyl}methionine methyl ester,
M.p. 191°-193° C.

N-{[4-(2-chlorophenyl)-thieno[4,2-f][1,4]diazepin-7-on-2-yl]carbonyl}-L-leucine methyl ester, M.p. 227° C.

Further thienodiazepine carboxylic acids are obtained as follows:

2-Carboxy-4-(2-chlorophenyl)-9-methyl-6H-thieno-[3,2-f][1,2,4]triazolo[4,3-a][1,4]diazepine (m.p. 302° C.) is obtained by the method described in German Offenlegungsschrift 2,503,235;

2-Carboxymethyl-4-(2-chlorophenyl)-9-methyl-6H-thieno-[3,2-f][1,2,4]triazolo[4,3-a][1,4]diazepine can be obtained in the following way:

Diethyl malonate and bromoacetaldehyde acetal provide, by processes known from the literature, dicarbethoxypropionaldehyde (boiling point 0.01: 92°-95° C.) which can be converted into the corresponding 2-aminobenzoylthiophene using chlorocyanoacetophenone and sulphur as in the example from the literature quoted for Example 16. Hydrolysis, decarboxylation and esterification with methanol/sulphuric acid provide 2-amino-3-(2-chlorobenzoyl)-5-(2-methoxycarbonylmethyl)thiophene. Bromoacetylation and amination result in the corresponding diazepinone of m.p. 180°-182° C. The thione prepared from this melts at 184°-185° C. Reaction with hydrazine followed by a ring-closure reaction with orthoacetic ester results in the methyl triazolothienocarboxylate of m.p. 139°-141° C. The latter is hydrolysed with aqueous alcoholic potassium hydroxide solution to give the free carboxylic acid of m.p. 257°-259° C.

4-[4-(2-Chlorophenyl)-9-methyl-6H-thieno[3,2-f][1,2,4]-triazolo[ 4,3-a][1,4]diazepin-2-yl]butan-1-carboxylic acid.

Starting from cycloheptanone it is possible to obtain, by a method known from the literature (L. Claisen, Ber.dtsch.chem.Ges. 40, (3907) the enol ether which is subjected to ozonolysis (V. Schmid, P. Grafen, Liebigs Ann. Chem. 656, 97 (1962)). This results in methyl 6-formylheptanoate (boiling point₁₅=115°-170° C.) which is reacted as already described to give the 2-amino-3-(2-chlorobenzoyl)-thiophen-2-butane carboxylic ester.

Methyl thienotriazolo-1,4-diazepin-2-butane carboxylate of m.p. 119°-121° C. is obtained analogously to the previous example. The acid of m.p. 133°-134° C. is obtained by hydrolysis.

5-Phenyl-7-(1-carboxyethyl)-1,3-dihydro-2H-[1,4]-benzodiazepin-2-one (m.p. 252°-255° C.) is obtained as described by M. Zinic et al., J. Heterocycl. Chem. 14, 1225 (1977).

Examples of some pharmaceutical compositions using compounds of the general formula I or II as active ingredient are indicated hereinafter. Unless expressly indicated otherwise, parts are parts by weight.

1. Tablets

The tablet contains the following ingredients:

| | |
|---|---|
| Active compound of formula I or II | 0.020 parts |
| Stearic acid | 0.010 parts |
| Dextrose | 1.890 parts |
| Total | 1.920 parts |

Preparation

The substances are mixed in a known manner and the mixture is compressed to form tablets, each of which weighs 1.92 g and contains 20 mg of active compound.

2. Ointment

The ointment is composed of the following ingredients:

| | |
|---|---|
| Active compound of formula I or II | 50 mg |
| Neribas ointment (commercial product from Scherax) | ad 10 g |

Preparation

The active compound is triturated with 0.5 g of ointment base, and the remaining base is gradually added in 1.0 g portions and intimately mixed to form an ointment. A 0.5% strength ointment is obtained. The dispersion of the active compound in the base is checked visually under the microscope.

3. Cream

| Composition: | |
|---|---|
| Active compound of formula I or II | 50 mg |
| Neribas ointment (commercial product from Scherax) | ad 10 g |

Preparation

The active compound is triturated with 0.5 g of cream base, and the remaining base is gradually incorporated in 1.0 g portions with a pestle. A 0.5% cream is obtained. The dispersion of the active compound in the base is checked visually under the microscope.

4. Ampoule solution

| Composition: | |
|---|---|
| Active compound of formula I or II | 1.0 mg |
| Sodium chloride | 45.0 mg |
| Water for injection | ad 5.0 ml |

Preparation

The active compound is dissolved and its own pH in water and sodium chloride is added as agent. The resulting solution is filtered to remove pyrogens, and the filtrate is dispensed under aseptic conditions into ampoules which are then sterilised and sealed. The ampoules contain 1 mg, 5 mg and 10 mg of active compound.

5. Suppositories

Each suppository contains:

| | |
|---|---|
| Active compound of formula I or II | 1.0 parts |
| Cocoa butter (m.p. 36-37° C.) | 1200.0 parts |
| Carnauba wax | 5.0 parts |

Preparation

The cocoa butter and carnauba wax are melted together. The active compound is added at 45° C., and stirring is continued until dispersion is complete. The mixture is poured into moulds of appropriate size, and the suppositories are packed as appropriate.

6. Inhalation solutions

| Composition | |
|---|---|
| a) Active compound of formula I or II | 500 mg |
| Na EDTA | 50 mg |
| Benzalkonium chloride | 25 mg |
| Sodium chloride | 880 mg |
| Distilled water | ad 100 ml |

Preparation

Na EDTA, benzalkonium chloride, sodium chloride and active compound are successively dissolved in 96% of the amount of water to form a clear solution to which the remainder of the water is added. The solution is dispensed into 20 ml dropping bottles. One dose (20 drops, 1 ml) contains 5 mg of active compound.

| b) Active compound of formula I or II | 500 mg |
|---|---|
| Sodium chloride | 820 mg |
| Distilled water | ad 100 ml |

Preparation

The active compound and sodium chloride are successively dissolved in 96% of the amount of water, the remaining water is added, and the solution is dispensed into single-dose containers (4 ml). The solution contains 20 mg of active compound.

Some $^1$H NMR data of selected compounds of the Examples in Table I are listed below:

EXAMPLE 4

$^1$H NMR (CD$_3$OD) δ (ppm)=7.23-8.33 (7H, m, aryl-H); 5.45 and 4.23 (2H, AB-Syst. $J_{AB}$=13 Hz, CH$_2$-7-ring); 4.23 (2H, s, CH$_2$—C=O); 3.45-3.90 (8H, m, morpholine-H); 2.68 (3H, s, CH$_3$-triazole).

EXAMPLE 5

$^1$H NMR (CDCl$_3$) δ (ppm)=7.21-8.21 (7H, m, aryl-H); 7.70 (1H, s, broad, NH); 5.49 and 4.17 (2H, AB-System, $J_{AB}$=13 Hz, CH$_2$-7-ring); 4.98 (1H, m, Asp-CH) 3.79 and 3.70 (6H, 2s, OCH$_3$); 3.05 (2H, m, Asp-CH$_2$CH); 2.64 (3H, s, CH$_3$-triazole).

EXAMPLE 6

$^1$H NMR (CDCl$_3$) δ (ppm)=7.16-8.32 (7H, m, aryl-H); 7.89 (1H, t, broad, NH) 7.59 (1H, s, broad, NH); 5.48 and 4.13 (2H, AB-syst. $J_{AB}$=13 Hz, CH$_2$-7-ring), 3.97-4.30 (4H, m, 2×CH$_2$—C=O); 3.26-3.85 (8H, m, morpholine-H); 2.62 (3H, s, CH$_3$-triazole).

EXAMPLE 11

$^1$H NMR (CDCl$_3$) δ (ppm)=7.14-8.26 (7H, m, aryl-H); 7.78 (1H, s, broad, NH); 5.49 and 4.09 (2H, AB-System, $J_{AB}$=13 Hz, CH$_2$-7-ring); 4.71 (1H, m, CH, thiophene ring); 1.95-3.62 (4H, m, CH$_2$CH$_2$-homothioserine lactone); 2.59 (3H, s, CH$_3$-triazole).

EXAMPLE 19

$^1$H NMR (CDCl$_3$) δ (ppm)=7.26-8.44 (8H, m, aryl-H);
8.30 (1H, s, broad, NH); 5.41 and 4.13 (2H, AB-Syst. $J_{AB}$=13 Hz, CH$_2$-7-ring); 4.21 (2H, s, Gly-CH$_2$); 3.40-3.89 (8H, m, morpholine-H); 2.70 (3H, s, CH$_3$-triazole).

EXAMPLE 21

$^1$H NMR (CD$_3$OD) δ (ppm)=7.47-8.40 (7H, m, aryl-H); 5.60 (2H, s, CH$_2$-7-ring); 4.41 (1H, s, CH—NH); 4.23 (2H, s, Gly-CH$_2$); 3.47-3.91 (8H, m, morpholine-H); 2.77 (3H, s, CH$_3$-triazole).

EXAMPLE 25

$^1$H NMR (CDCl$_3$) δ (ppm)=7.17-8.16 (7H, m, aryl-H); 5.55 and 4.15 (2H, AB-Syst., $J_{AB}$=13 Hz, CH$_2$-7-ring); 7.59 (1H, s, broad, NH), 5.33 (1H, m, CH); 3.45-3.94 (8H, m, morphiline-H); 3.16 (2H, t, J =6.5 Hz, SO$_2$CH$_2$), 2.94 (3H, s, SO$_2$CH$_3$); 2.64 (3H, s, CH$_3$-triazole); 2.32 (2H, m, CH$_2$—CH).

EXAMPLE 27

$^1$H NMR (CDCl$_3$) δ (ppm)=7.02-8.20 (7H, m, aryl-HO; 7.16 (1H, d, J=8 Hz, ; 6.01 (1H, d, J=8 Hz, —CO—NHiPr); 5.51 and 4.13 (2H, AB-System, $J_{AB}$=13 Hz, CH$_2$-7-ring); 3.80-4.47 (2H, m, NH—CH, Val-α-CH); 2.62 (3H, s, CH$_3$-triazole); 2.09 (1H, m, CH—CH(CH$_3$)$_2$); 1.12 and 1.18 (6H, 2d, J=6 Hz, (CH—C)$_2$—CH—C); 0.97 (6H, d, J=7 Hz, (CH$_3$)$_2$—CH—N).

EXAMPLE 31

$^1$H NMR (CDCl$_3$) δ (ppm)=7.09-7.61 (5H, m, aryl-H; NH); 7.18 (1H, s, thiophene-H); 5.08 (1H, m, Leu-CH); 4.95 (2H, s, CH$_2$-7-ring); 3.36-3.90 (8H, m, morphiline-H); 2.75 (3H, s, CH$_3$-triazole); 1.36-1.87 (3H, m, CH$_2$—CH); 0.93 and 1.00 (6H, 2d, J=8 Hz, (CH$_3$)$_2$—C);

EXAMPLE 35

$^1$H NMR (CDCl$_3$) δ (ppm) β 7.14-8.20 (8H, m, aryl-HNH); 5.52 and 4.13 (2H, AB-System, $J_{AB}$=13 Hz, CH$_2$-7-ring); 4.83 (1H, m, ala-α-CH); 3.27-3.80 (5H, 2×N—CH$_2$—, —CH-cyclopropane); 1.43 (3H, d, J=6 Hz, CH$_3$—CH); 0.88-2.28 (8H, m, CH$_2$-pyrrolidine, CH$_2$-cyclopropane).

EXAMPLE 38

$^1$H NMR (CDCl$_3$) δ (ppm)=7.20-8.22 (7H, m, aryl-H); 5.54 and 4.14 (2H, AB-System, $J_{AB}$=13 Hz CH$_2$-7-ring); 5.23 (1H, dd, CH); 7.37 1H, s, broad, NH); 3.50-3.92 (8H, m, morphiline-H); 2.64 (3H, s, CH$_3$- triazole); 2.57 (2H, t, J=7 Hz, SCH₂); 2.07 (3H, s, SCH₃); 2.01 (2H, m, CH₂—CH).

EXAMPLE 42

¹H NMR (CDCl₃) δ (ppm)=7.13-8.30 (7H, m, aryl-H); 7.90 (1H, t, NH—CH₂—C=O); 6.7 (1H, t, broad, NH—CH₂—C=C); 5.49 and 4.13 (2H, AB-Syst., $J_{AB}$=13 Hz, CH₂-7-ring); 4.98-6.10 (3H, m, CH₂=CH—); 3.98-4.17 (2H, m, CH₂—C=); 3.89 (2H, t, J=6 Hz, Gly-CH₂); 2.61 (3H, s, CH₃-triazole).

EXAMPLE 44

¹H NMR (CDCl₃) δ (ppm)=7.23-7.60 (4H, m, aryl-H); 6.92 (1H, t, J=3 Hz, NH); 4.95 (2H, s, CH₂-7-ring); 4.09 (2H, d, J=3 Hz, Gly-CH₂); 3.80 (2H, s, CH₂—C=O); 3.25-3.92 (8H, m, morpholine-H); 2.74 (3H, s, CH₃-triazole).

EXAMPLE 48

¹H NMR (CDCl₃) δ (ppm)=7.20-7.61 (4H, m, aryl-H); 6.66 (1H, t, J=4 Hz, NH); 6.44 (1H, s, thiophene-H); 4.93 (2H, s, CH₂-7-ring); 4.05 (2H, d, J=4 Hz, Gly-CH₂); 3.28-3.83 (8H, m, morpholine-H); 3.15 (2H, t, J=6.5 Hz, CH₂-thiophene); 2.61 (2H, t, j=6.5 Hz, CH₂—C=O); 2.70 (3H, s, CH₃-triazole).

What we claim is:

1. A compound of formula

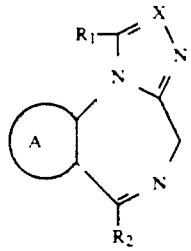

I or

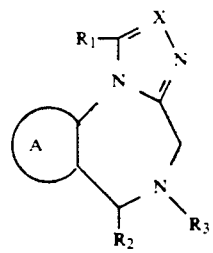

II in which
X is CH, C-halogen or nitrogen;
R₁ is hydrogen, branched or unbranched C₁-C₄ alkyl optionally substituted by hydroxyl or halogen, cyclopropyl, C₁-C₄ alkoxy or halogen;
R₂ is phenyl, α-pyridyl or phenyl substituted with one or more substituents selected from methyl, methoxy, halogen, nitro and trifluoromethyl;
R₃ is hydrogen or branched or unbranched C₁-C₄ alkyl;
A is a fused-on ring of the formula

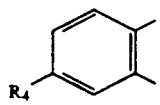

a or

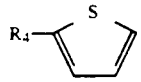

b in which
R₄ is a functional side-chain of the formula

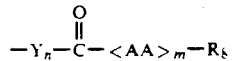

in which
n is zero or an integer from 1 to 8;
m is an integer from 1 to 3;
y is a branched or unbranched alkyl with n carbons;
<AA> is an amino acid linked N-terminally of the formula

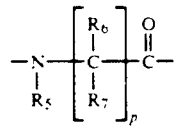

where
p is an integer from 1 to 8;
R₅ is hydrogen or branched or unbranched C₁-C₅ alkyl; and
R₆ and R₇, which can be identical or different, are each hydrogen, alkenyl or alkynyl having 1 to 10 carbons, C₃-C₆ cycloalkyl, or phenyl, said phenyl being optionally substituted with at least one substituent selected from hydroxyl, halogen, amino, and branched or unbranched C₁-C₄ alkylamino, d-(C₁-C₄) alkylamino or C₁-C₄ alkoxy,
or
R₆ and R₇, which can be identical or different, are each branched or unbranched alkyl with 1 to 10 carbons, which may be substituted one or more times by hydroxyl, C₁-C₄ alkoxy, C₃-C₇ cycloalkyl, halogen, amino, (which can optionally be substituted once or twice by branched or unbranched alkyl, alkoxycarbonyl or aralkoxycarbonyl, in each case having 1 to 4 carbon atoms in the alkyl chain), guanidino, ureido, carboxy, C₁-C₄ alkoxycarbonyl, cyano, aminocarbonyl, C₁-C₄ alkylcarbonyl, mercapto, C₁-C₄ alkylthio, benzylthio, C₁-C₄ alkylsulfinyl, C₁-C₄ alkylsulfonyl, 3-indolyl, imidazolyly, pyrazolyl, or an amide of the formula

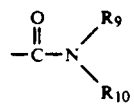

in which
R₉ and R₁₀, which can be identical or different, are each hydrogen, branched or unbranched alkyl, alkenyl or alkynyl having 1 to 4 carbons, C₁-C₄ alkyl substituted by amino which can optionally be substituted once or twice with branched or unbranched C₁-C₄ alkyl in the alkyl chain or once with hydroxyl, or R9 and R10 together form a 5- to 6-membered ring selected from pyrrol, pyrrolin, pyrrolidin, 2-methylpyrrolidin, 3-methylpyrrolidin, piperidin, piperazin, N-methylpiperazin, N-ethylpiperazin, N-n-propyl-piperazin, N-benzylpiperazin, morpholin, thiomorpholin, imidazol, imidazolin, imidazolidin, triazol, pyrazol, pyrazolin, pyrazolidin, triazin, 1,2,3,4-tetrazin, 1,2,3,5-tetrazin, 1,2,4,5-tetrazin, said ring being optionally substituted with at least one branched or unbranched $C_1-C_4$ alkyl;

$R_8$ is an amino of the formula

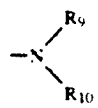

or branched or unbranched $C_1-C_4$ alkoxy or $C_1-C_4$ alkylthio, the alkyl of which can be optionally substituted with an amino of the formula

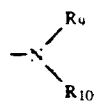

in which $R_9$ and $R_{10}$, singly or together, are as previously defined $R_6$ and $R_7$, taken together optionally form a 3- to 7-membered carbocyclic ring, said ring being optionally substituted with at least one branched or unbranched $C_1-C_4$ alkyl; or $R_5$ taken together with $R_6$ or $R_7$, optionally form a 4- to 7-membered carbocyclic ring, said ring being optionally substituted with at least one branched or unbranched $C_1-C_4$ alkyl; or $R_7$ taken together with $R_8$ optionally form a 5- to 7-membered ring of the formula

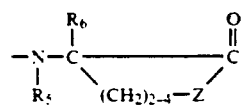

in which $R_5$ and $R_6$ are as previously defined; and Z is one of the heteroatoms, oxygen or sulphur, or Z is NH;

and the optically active isomers, racemates and physiologically acceptable acid addition salts thereof.

2. A compound of formula I or II in claim 1 wherein:

X is CH or nitrogen;

A is as defined in claim 1;

$R_1$ is hydrogen, methyl, ethyl, cyclopropyl, methoxy, ethoxy, chlorine or bromine;

$R_2$ is phenyl or 2-halophenyl;

$R_3$ is hydrogen;

$R_4$ is a functional side-chain of the formula

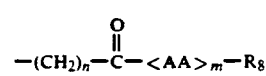

in which n is zero or 1 when A is the fused-on ring of formula a, and is zero, 1, 2, 3 or 4 when A is the fused-on ring of formula b;

m is 1 or 2;

<AA> is an α-amino acid of the formula

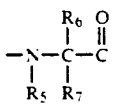

in which $R_5$ is hydrogen $R_6$ and $R_7$, which can be identical or different, are each hydrogen, branched or unbranched $C_1-C_8$ alkyl optionally substituted with $C_1-C_4$ alkoxycarbonyl, $C_1-C_4$ alkylthio or $C_1-C_4$ alkylsulfonyl;

$R_8$ is $C_1-C_4$ alkoxy or an amino of the formula

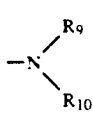

in which $R_9$ and $R_{10}$, which can be identical or different, are each branched or unbranched alkyl or alkenyl having 1 to 4 carbons, or $R_9$ and $R_{10}$ together form a 5- or 6-membered ring optionally substituted with at least one branched or unbranched $C_1-C_4$ alkyl and the optically active isomers, racemates and physiologically acceptable acid addition salts thereof.

3. A compound of formula I or II in claim 1 wherein:

X is CH or nitrogen;

$R_1$, $R_3$ and A are respectively defined in claim 1;

$R_2$ is phenyl or halophenyl;

$R_4$ is a functional side-chain of the formula

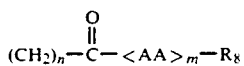

in which n, m and $R_8$ are respectively defined in claim 1; and <AA> is an amino acid of the formula

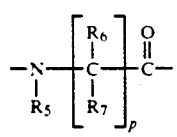

in which

P is 1 or 2; and $R_5$, $R_6$ and $R_7$ are respectively defined in claim 1;

and the optically active isomers, racemates, and physiologically acceptable acid addition salts thereof.

4. A compound of claim 3 wherein the halophenyl of $R_2$ is 2-halophenyl.

5. A compound of claim 3 wherein the halophenyl of $R_2$ is 2-chlorophenyl.

6. A compound of claim 3 wherein m is 1.

7. A compound of formula I or II in claim 1 wherein:

X is CH or nitrogen;

A is as defined in claim 1;

$R_1$ is hydrogen, methyl, ethyl, cyclopropyl, methoxy, ethoxy, or halogen;

$R_2$ is phenyl or 2-halophenyl;

$R_3$ is hydrogen or methyl;

$R_4$ is a functional side-chain of the formula

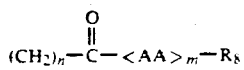

in which n is zero or 1 when A is the fused-on ring of formula a, and is zero or an integer from 1 to 8 when A is the fused-on ring of formula b;
m is 1 or 2;
$R_8$ is as defined in claim 1;
<AA> is an amino acid of the formula

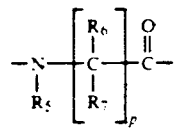

in which
p is 1 or 2; and
$R_5$, $R_6$ and $R_7$ are respectively defined in claim 1; and the optically active isomers, racemates and physiologically acceptable acid addition salts thereof.

8. A compound of claim 7 wherein the halogen of $R_1$ is chlorine or bromine.

9. A compound of claim 7 wherein the 2-halophenyl of $R_2$ is 2-chlorophenyl.

10. A compound of claim 7 wherein $R_3$ is hydrogen.

11. A compound of claim 7 wherein m is 1.

12. A compound of claim 2 wherein X is nitrogen.

13. A compound of claim 2 wherein $R_1$ is methyl or methoxy.

14. A compound of claim 2 wherein the 2-halophenyl of $R_2$ is 2-chlorophenyl.

15. A compound of claim 2 wherein n is zero when A is the fused-on ring of formula a.

16. A compound of claim 2 wherein n is zero, 1 or 2 when A is the fused-on ring of formula b.

17. A compound of claim 2 wherein the alkyl of $R_6$ or $R_7$ is $C_1$-$C_5$ alkyl.

18. A compound of claim 2 wherein $R_8$ is methoxy or ethoxy.

19. A compound of formula I or II in claim 1 wherein <AA> of $R_4$ is an amino acid selected from Aad, Y-Abu, ε-Aca, Ach, Acp, β-Aib, Δ-Ala, Ama, Apm, Apr, Arg, Asn, Asu, Cys, Gln, Glu, His, Ser, Hyl, Hyp, 3-Hyp, Ise, Lys, Nle, Nva, Pec, Phe, Phg, Pic, Pro, Tle, Pyr, Ser, Thr, Tyr, Trp, Ala, β-Ala, Gly, Val, Met, Asp, Sar, Met-(O₂), Aib, Abu, Ile, or Leu.

20. A compound of formula I or II in claim 1 wherein <AA> of $R_4$ is an amino acid selected from Ala, β-Ala, Gly, Val, Met, Asp, Sar, Met-(O₂), Aib, Abu, Ile or Leu.

21. The methylamide of N-{[1-methyl-6-(2-chlorophenyl)-4H-[1,2,4]triazolo[4,3-a][1,4]-benzodiazepin-8-yl]-carbonyl}-D,L-alanine 22. The dimethylamide of N-{[1-methyl-6-(2-chlorophenyl)-4H-[1,2,4]triazolo[4,3-a][1,4]-benzodiazepin-8-yl]carbonyl}-1-aminocyclohexan-1-carboxylic acid.

23. The dimethylamide of N-{[1-methyl-6-(2-chlorophenyl)-4H-[1,2,4]triazolo[4,3-a][1,4]-benzodiazepin-8-yl]carbonyl}-L-isoleucine.

24. The dimethylamide of N-{[1-methyl-6-(2-chlorophenyl)-4H-[1,2,4]triazolo[4,3-a][1,4]-benzodiazepin-8-yl]carbonyl-L-aspartic acid 25. The morpholide of N-{[1-methyl-6-(2-chlorophenyl)-4H-[1,2,4]triazolo[4,3-a][1,4]-benzodiazepin-8-yl]carbonyl}-D,L-β-aminoisobuteric acid.

26. The morpholide of N-{2-[1-methoxy-6-(2-chlorophenyl)-4H-[1,2,4]triazolo[4,3-a][1,4]-benzodiazepin-8-yl]propionyl}-L-serine.

27. The diethylamide of N-{2-[1-methoxy-6-(2-chloro-phenyl)-4H-[1,2,4]triazolo[4,3-a][1,4]-benzodiazepin-8-yl]propionyl}-α-methylalanine.

28. The morpholide of N-{2-[4-(2-chlorophenyl)-9-methyl-6H-thieno[3,2-f]imidazo[1,2-a][1,4]diazepin-2-yl]propionyl}-glycine.

29. The diethylamide of N-{2-[1-methyl-6-phenyl-4H-[1,2,4]triazolo[4,3-a][1,4]benzodiazepin-8-yl]-propionyl}-L-alanine.

30. The dimethylamide of N-{3-[4-(2-chlorophenyl)-9-methyl-6H-thieno[3,2-f]imidazo[1,2-a][1,4]-diazepin-2-yl]-2-methylpropionyl}-D,L-α-amino-propionic acid.

31. A compound of the formula

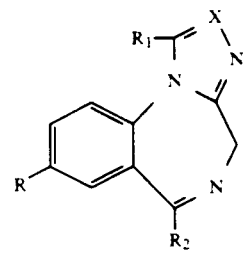

or

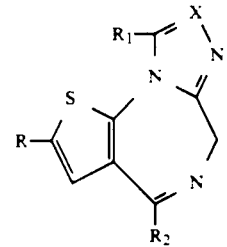

in which R is a side claim of the formula

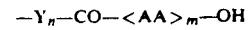

and $R_1$, $R_2$, X, Y, n, m and <AA> are respectively defined in claim 1.

32. A compound of the formula

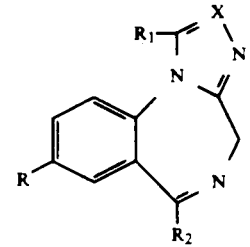

or

-continued
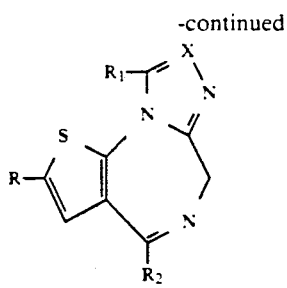
in which R is a side-chain of the formula
$$-Y_n-COOR-$$
in which R' is hydrogen or branched or unbranched $C_1-C_2$ alkyl, and $R_1$, $R_2$, X. Y. and n are respectively defined in claim 1.
* * * * *